US008378130B2

(12) United States Patent
Boulos et al.

(10) Patent No.: US 8,378,130 B2
(45) Date of Patent: Feb. 19, 2013

(54) PRODUCT CONTAINING EPICHLOROHYDRIN, ITS PREPARATION AND ITS USE IN VARIOUS APPLICATIONS

(75) Inventors: Noel Boulos, Houston, TX (US); Philippe Krafft, Rhode Saint Genese (BE); Patrick Gilbeau, Braine-le-Comte (BE); Dominique Balthasart, Brussels (BE)

(73) Assignee: SOLVAY (Societe Anonyme), Brussels (BE)

( * ) Notice: Subject to any disclaimer, the term of this patent is extended or adjusted under 35 U.S.C. 154(b) by 341 days.

(21) Appl. No.: 12/663,744

(22) PCT Filed: Jun. 11, 2008

(86) PCT No.: PCT/EP2008/057246
§ 371 (c)(1),
(2), (4) Date: Jun. 11, 2008

(87) PCT Pub. No.: WO2008/152044
PCT Pub. Date: Dec. 18, 2008

(65) Prior Publication Data
US 2010/0179300 A1   Jul. 15, 2010

Related U.S. Application Data

(60) Provisional application No. 61/007,661, filed on Dec. 14, 2007, provisional application No. 61/013,672, filed on Dec. 14, 2007.

(30) Foreign Application Priority Data

Jun. 12, 2007 (FR) ...................... 07 55696
Sep. 21, 2007 (FR) ...................... 07 57751

(51) Int. Cl.
C07D 301/32 (2006.01)
(52) U.S. Cl. ........ 549/541; 549/516; 549/518; 549/524; 549/525
(58) Field of Classification Search .................. 549/518, 549/516, 524, 525
See application file for complete search history.

(56) References Cited

U.S. PATENT DOCUMENTS

| 280,893 A | 7/1883 | Baujard |
| 865,727 A | 9/1907 | Queneau |
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,505,735 A | 4/1950 | Halbedel |
| 2,726,072 A | 12/1955 | Herman |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,052,612 A | 9/1962 | Henegar et al. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,879,180 A | 4/1975 | Hutgens et al. |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,127,594 A | 11/1978 | Anderson et al. |
| 4,173,710 A | 11/1979 | Boulet et al. |

(Continued)

FOREIGN PATENT DOCUMENTS

| BE | 422877 | 8/1937 |
| CN | 1296003 A | 5/2001 |
| CN | 101041421 | 9/2007 |
| DD | 216471 A1 | 12/1984 |
| DE | 58396 C | 8/1891 |

(Continued)

OTHER PUBLICATIONS

Horsley, Lee H.—"Azeotropic Data-III", The Dow Chemical Co., Midland, MI, American Chemical Society 1973; pp. 1-4; 4 pgs.
Suzawa, Yoshikazu, et al—"Incineration System for Waste Liquid Containing Chlorinated Organic Compounds", Chemical Apparatuses, 1981, vol. 23, No. 11; 34 pgs; Translation in English provided.

(Continued)

Primary Examiner — Gregory Listvoyb
(74) Attorney, Agent, or Firm — Oblon, Spivak, McClelland, Maier & Neustadt, L.L.P.

(57) ABSTRACT

Product containing epichlorohydrin and at least one alkyl glycidyl ether in an amount of less than 0.1 g/kg of product. Use of the product containing epichlorohydrin in the manufacture of epoxy resins, of glycidyl ethers, of glycidyl esters, of glycidyl amides, of glycidyl imides, of products that will be used in food and drink applications, of cationization agents, and of flame retardants, of products which will be used as detergent ingredient and of epichlorohydrin oligomers.

19 Claims, 6 Drawing Sheets

U.S. PATENT DOCUMENTS

| | | | |
|---|---|---|---|
| 4,197,399 A | 4/1980 | Noel et al. |
| 4,220,529 A | 9/1980 | Daude-Lagrave |
| 4,240,885 A | 12/1980 | Suciu et al. |
| 4,255,470 A | 3/1981 | Cohen et al. |
| 4,294,776 A | 10/1981 | Hardy et al. |
| 4,309,394 A | 1/1982 | Hudson |
| 4,390,680 A | 6/1983 | Nelson |
| 4,405,465 A | 9/1983 | Moore et al. |
| 4,415,460 A | 11/1983 | Suciu et al. |
| 4,464,517 A | 8/1984 | Makino et al. |
| 4,499,255 A | 2/1985 | Wang et al. |
| 4,560,812 A | 12/1985 | Blytas |
| 4,595,469 A | 6/1986 | Foller |
| 4,599,178 A | 7/1986 | Blytas |
| 4,609,751 A | 9/1986 | Hajjar |
| 4,634,784 A | 1/1987 | Nagato et al. |
| 4,655,879 A | 4/1987 | Brockmann et al. |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,169,964 A * | 12/1992 | Jakobson et al. ............. 549/541 |
| 5,200,163 A | 4/1993 | Henkelmann et al. |
| 5,278,260 A | 1/1994 | Schaffner et al. |
| 5,286,354 A | 2/1994 | Bard et al. |
| 5,344,945 A | 9/1994 | Grunchard |
| 5,359,094 A | 10/1994 | Teles et al. |
| 5,393,428 A | 2/1995 | Dilla et al. |
| 5,445,741 A | 8/1995 | Dilla et al. |
| 5,478,472 A | 12/1995 | Dilla et al. |
| 5,486,627 A | 1/1996 | Quarderer, Jr. et al. |
| 5,567,359 A | 10/1996 | Cassidy et al. |
| 5,578,740 A | 11/1996 | Au et al. |
| 5,679,839 A | 10/1997 | Armand et al. |
| 5,710,350 A | 1/1998 | Jeromin et al. |
| 5,731,476 A | 3/1998 | Shawl et al. |
| 5,744,655 A | 4/1998 | Thomas et al. |
| 5,779,915 A | 7/1998 | Becker et al. |
| 5,908,946 A | 6/1999 | Stern et al. |
| 5,993,974 A | 11/1999 | Fukushima et al. |
| 6,024,829 A | 2/2000 | Easter et al. |
| 6,103,092 A | 8/2000 | Silva |
| 6,111,153 A | 8/2000 | Crow et al. |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 * | 9/2001 | Strebelle et al. ............. 549/518 |
| 6,288,287 B2 | 9/2001 | Ueoka et al. |
| 6,350,888 B1 | 2/2002 | Strebelle et al. |
| 6,350,922 B1 | 2/2002 | Vosejpka et al. |
| 6,521,794 B2 | 2/2003 | Hirota |
| 6,719,957 B2 | 4/2004 | Brady, Jr. et al. |
| 6,740,633 B2 | 5/2004 | Norenberg et al. |
| 6,806,396 B2 | 10/2004 | Gelblum et al. |
| 6,831,201 B2 | 12/2004 | Katsuura et al. |
| 7,126,032 B1 | 10/2006 | Aiken |
| 7,128,890 B2 | 10/2006 | Ollivier |
| 7,557,253 B2 | 7/2009 | Gilbeau |
| 7,584,629 B2 | 9/2009 | Sohn et al. |
| 7,615,670 B2 | 11/2009 | Gilbeau |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0047781 A1 | 3/2004 | Becenel, Jr. |
| 2004/0150123 A1 | 8/2004 | Strofer et al. |
| 2004/0179987 A1 | 9/2004 | Oku et al. |
| 2004/0232007 A1 | 11/2004 | Carson et al. |
| 2005/0115901 A1 | 6/2005 | Heuser et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0293707 A1 | 12/2007 | Wolfert et al. |
| 2008/0053836 A1 | 3/2008 | Bulan et al. |
| 2008/0146753 A1 | 6/2008 | Woike et al. |
| 2008/0154050 A1 | 6/2008 | Gilbeau |
| 2008/0161613 A1 | 7/2008 | Krafft et al. |
| 2008/0194847 A1 | 8/2008 | Krafft et al. |
| 2008/0194849 A1 | 8/2008 | Krafft et al. |
| 2008/0194851 A1 | 8/2008 | Gilbeau |
| 2008/0200642 A1 | 8/2008 | Krafft |
| 2008/0200701 A1 | 8/2008 | Krafft et al. |
| 2008/0207930 A1 | 8/2008 | Gilbeau et al. |
| 2008/0214848 A1 | 9/2008 | Krafft et al. |
| 2008/0281132 A1 | 11/2008 | Krafft et al. |
| 2009/0022653 A1 | 1/2009 | Strebelle et al. |
| 2009/0131631 A1 | 5/2009 | Krafft et al. |
| 2009/0173636 A1 | 7/2009 | Ooms et al. |
| 2009/0198041 A1 | 8/2009 | Krafft et al. |
| 2009/0270588 A1 | 10/2009 | Krafft et al. |
| 2009/0275726 A1 | 11/2009 | Krafft et al. |
| 2010/0029959 A1 | 2/2010 | Fan et al. |
| 2010/0032617 A1 | 2/2010 | Gilbeau et al. |
| 2010/0105862 A1 | 4/2010 | Krafft et al. |
| 2010/0105964 A1 | 4/2010 | Krafft et al. |
| 2011/0028683 A1 | 2/2011 | Gilbeau et al. |

FOREIGN PATENT DOCUMENTS

| | | |
|---|---|---|
| DE | 180668 C | 1/1906 |
| DE | 197308 C | 11/1906 |
| DE | 238341 C | 3/1908 |
| DE | 197309 C | 4/1908 |
| DE | 869 193 | 3/1953 |
| DE | 1041488 B | 10/1958 |
| DE | 1075103 B | 2/1960 |
| DE | 1226554 B | 10/1966 |
| DE | 2 241 393 | 2/1974 |
| DE | 25 21 813 | 12/1975 |
| DE | 3003819 A1 | 8/1981 |
| DE | 3243617 | 5/1984 |
| DE | 3721003 C1 | 12/1988 |
| DE | 43 02 306 | 8/1994 |
| DE | 4335311 A1 | 4/1995 |
| DE | 10203914 C1 | 10/2003 |
| DE | 10254709 A1 | 6/2004 |
| EP | 0 296 341 | 12/1988 |
| EP | 0347618 A2 | 12/1989 |
| EP | 0358255 A1 | 3/1990 |
| EP | 0421379 A1 | 4/1991 |
| EP | 0 452 265 | 10/1991 |
| EP | 0518765 A1 | 12/1992 |
| EP | 0522382 A1 | 1/1993 |
| EP | 0535949 B1 | 4/1993 |
| EP | 0561441 A1 | 9/1993 |
| EP | 0563720 A1 | 10/1993 |
| EP | 0568389 A1 | 11/1993 |
| EP | 0582201 A2 | 2/1994 |
| EP | 0 618 170 | 10/1994 |
| EP | 0 916 624 | 5/1999 |
| EP | 0919551 A1 | 6/1999 |
| EP | 0 774 450 | 2/2000 |
| EP | 1059278 A2 | 12/2000 |
| EP | 1106237 A1 | 6/2001 |
| EP | 1153887 A2 | 11/2001 |
| EP | 1163946 A1 | 12/2001 |
| EP | 1231189 A1 | 8/2002 |
| EP | 1298154 A1 | 4/2003 |
| EP | 1411027 A1 | 4/2004 |
| EP | 1752435 A1 | 2/2007 |
| EP | 1752436 A1 | 2/2007 |
| EP | 1760060 A1 | 3/2007 |
| EP | 1762556 A1 | 3/2007 |
| EP | 1770081 A1 | 4/2007 |
| EP | 1772446 A1 | 4/2007 |
| EP | 1775278 A1 | 4/2007 |
| EP | 2085364 | 8/2009 |
| FR | 1 306 231 | 10/1961 |
| FR | 1 417 388 | 10/1964 |
| FR | 1476073 A | 4/1967 |
| FR | 1 577 792 | 8/1968 |
| FR | 2151107 | 4/1973 |
| FR | 2180138 | 5/1973 |
| FR | 2 217 372 | 2/1974 |
| FR | 2565229 A1 | 12/1985 |

| | | |
|---|---|---|
| FR | 2752242 A1 | 2/1998 |
| FR | 2862644 A1 | 5/2005 |
| FR | 2868419 A1 | 10/2005 |
| FR | 2869612 A1 | 11/2005 |
| FR | 2869613 A1 | 11/2005 |
| FR | 2872504 A1 | 1/2006 |
| FR | 2881732 A1 | 8/2006 |
| FR | 2885903 A1 | 11/2006 |
| FR | 2 912 743 | 8/2008 |
| FR | 2913683 | 9/2008 |
| FR | 2913683 A1 | 9/2008 |
| FR | 2 917 411 | 12/2008 |
| FR | 2918058 A1 | 1/2009 |
| FR | 2925045 A1 | 6/2009 |
| FR | 2929611 A1 | 10/2009 |
| FR | 2935699 A1 | 3/2010 |
| FR | 2935968 A1 | 3/2010 |
| GB | 14767 A | 0/1914 |
| GB | 406345 | 8/1932 |
| GB | 404938 A | 1/1934 |
| GB | 467481 A | 6/1937 |
| GB | 541357 A | 11/1941 |
| GB | 679536 A | 9/1952 |
| GB | 702143 A | 1/1954 |
| GB | 736641 A | 9/1955 |
| GB | 799567 A | 8/1958 |
| GB | 1046521 | 1/1964 |
| GB | 984446 A | 2/1965 |
| GB | 984633 A | 3/1965 |
| GB | 1083594 A | 9/1967 |
| GB | 1286893 A | 8/1972 |
| GB | 1387668 A | 3/1975 |
| GB | 1 493 535 | 4/1975 |
| GB | 1414976 A | 11/1975 |
| GB | 2173496 A | 10/1986 |
| GB | 2336584 A | 10/1999 |
| HU | 2002-003023 | 3/2004 |
| JP | 3927230 B2 | 11/1939 |
| JP | 50-062909 | 5/1975 |
| JP | 51021635 B | 7/1976 |
| JP | 55041858 A | 3/1980 |
| JP | 5629572 | 3/1981 |
| JP | 5699432 | 8/1981 |
| JP | 56-155009 | 12/1981 |
| JP | 60-258171 | 12/1985 |
| JP | 61-044833 | 3/1986 |
| JP | 61 112066 A | 5/1986 |
| JP | 61-140532 | 6/1986 |
| JP | 61-236749 | 10/1986 |
| JP | 62242638 A | 10/1987 |
| JP | 63195288 A | 8/1988 |
| JP | 2-137704 | 5/1990 |
| JP | 03014527 A | 1/1991 |
| JP | 03223267 A | 10/1991 |
| JP | 3223267 A | 10/1991 |
| JP | 04089440 A | 3/1992 |
| JP | 04-217637 | 8/1992 |
| JP | 06-009589 | 1/1994 |
| JP | 625196 B2 | 4/1994 |
| JP | 06184024 A | 7/1994 |
| JP | 6321852 A | 11/1994 |
| JP | 08-003087 | 1/1996 |
| JP | 859593 | 3/1996 |
| JP | 09-2999953 | 11/1997 |
| JP | 10139700 A | 5/1998 |
| JP | 10-218810 | 8/1998 |
| JP | 1998218810 A | 8/1998 |
| JP | 20000344692 A | 12/2000 |
| JP | 2001/037469 | 2/2001 |
| JP | 2001-213827 A | 8/2001 |
| JP | 2001-261308 | 9/2001 |
| JP | 2001-1261581 A | 9/2001 |
| JP | 2001-276572 | 10/2001 |
| JP | 2002-02033 A2 | 1/2002 |
| JP | 20020038195 A | 2/2002 |
| JP | 20020265986 A | 9/2002 |
| JP | 2002-363153 A | 12/2002 |
| JP | 2003-89680 A | 3/2003 |
| JP | 2003081891 A | 3/2003 |
| JP | 2003-183191 | 7/2003 |
| JP | 2003-206473 | 7/2003 |
| JP | 2004-518102 | 6/2004 |
| JP | 2004-216246 | 8/2004 |
| JP | 2005007841 A2 | 1/2005 |
| JP | 2005097177 A2 | 4/2005 |
| JP | 2005-513064 | 5/2005 |
| JP | 2007-008898 | 1/2007 |
| JP | 2009-263338 | 11/2009 |
| KR | 900006513 | 11/1987 |
| KR | 1019920003099 B1 | 4/1992 |
| KR | 10-514819 B1 | 9/2005 |
| PL | 136598 | 3/1986 |
| PL | 162910 | 1/1994 |
| SU | 123153 | 1/1959 |
| SU | 1125226 | 11/1984 |
| SU | 1159716 | 6/1985 |
| SU | 1685969 | 10/1991 |
| WO | WO 95/14639 | 6/1995 |
| WO | WO 96/15980 | 5/1996 |
| WO | WO 97/48667 | 12/1997 |
| WO | WO 96/07617 | 3/1998 |
| WO | WO 98/37024 | 8/1998 |
| WO | WO 99/14208 | 3/1999 |
| WO | WO 9932397 A1 | 7/1999 |
| WO | WO 0024674 A1 | 5/2000 |
| WO | WO 0141919 A1 | 6/2001 |
| WO | WO 0186220 A2 | 11/2001 |
| WO | WO 2002/026672 A2 | 4/2002 |
| WO | WO 02/059536 | 8/2002 |
| WO | WO 03/064357 | 8/2003 |
| WO | WO 2004/056758 | 7/2004 |
| WO | WO 2005021476 A1 | 3/2005 |
| WO | WO 2005054167 A1 | 6/2005 |
| WO | WO 2005/097722 | 10/2005 |
| WO | WO 2005/115954 | 12/2005 |
| WO | WO 2005/116004 | 12/2005 |
| WO | WO 2006020234 A1 | 2/2006 |
| WO | WO 2006/100311 A2 | 9/2006 |
| WO | WO 2006/100312 A2 | 9/2006 |
| WO | WO 2006/100313 A2 | 9/2006 |
| WO | WO 2006/100314 A1 | 9/2006 |
| WO | WO 2006/100315 A2 | 9/2006 |
| WO | WO 2006/100316 A1 | 9/2006 |
| WO | WO 2006/100317 A1 | 9/2006 |
| WO | WO 2006/100318 A2 | 9/2006 |
| WO | WO 2006/100319 A1 | 9/2006 |
| WO | WO 2006/100320 A2 | 9/2006 |
| WO | WO 2006/106153 A2 | 10/2006 |
| WO | WO 2006/106154 A1 | 10/2006 |
| WO | WO 2006/106155 A2 | 10/2006 |
| WO | WO 2007/054505 A2 | 5/2007 |
| WO | WO2007/144335 | 12/2007 |
| WO | WO 2008/101666 | 8/2008 |
| WO | WO2008/107468 | 9/2008 |
| WO | WO 2008/110588 | 9/2008 |
| WO | WO2008/145729 | 12/2008 |
| WO | WO 2008/147473 | 12/2008 |
| WO | WO 2008/152043 | 12/2008 |
| WO | WO 2008/152045 | 12/2008 |
| WO | WO 2009/000773 | 12/2008 |
| WO | WO 2009/016149 A2 | 2/2009 |
| WO | WO 2009026212 A1 | 2/2009 |
| WO | WO2009/043796 A1 | 4/2009 |
| WO | WO 2009/077528 | 6/2009 |
| WO | WO 2009/077528 A1 | 6/2009 |
| WO | WO 2009/095429 A1 | 8/2009 |
| WO | WO 2009/121853 | 10/2009 |
| WO | WO2009/121853 A1 | 10/2009 |
| WO | WO 2010/029039 | 3/2010 |
| WO | WO 2010/029039 A1 | 3/2010 |
| WO | WO 2010/029153 | 3/2010 |
| WO | WO 2010/029153 A1 | 3/2010 |
| WO | WO 2010/066660 | 6/2010 |

OTHER PUBLICATIONS

D'Alonzo, R.P., et al—"Glyceride Composition of Processed Fats and Oils As Determined by Glass Capillary Gas Chromatography", Journal of American Oil Chemists' Society, 1982, vol. 59, No. 7, pp. 292-295; 4 pgs.
Chemical Engineering Handbook, 6th Revised Edition, 2001, pp. 1-36; 56 pgs; Translation in English provided.
"Electrolytic cell test for electrolysis of epoxy sewage salt to prepare chlor-alkali", Process Equipment Department of Research Institute of Chloro-Alkali, Shengyang Chemical Plant, Liaoning Chemical Industry, Issue No. 2, pp. 32-37, published Dec. 31, 1981; 17 pgs; Translation in English provided.
Chengxin, Ren, et al—"Analysis on the Composition of the Byproduct During the Manufacturing Process of S-Epichlorohydrin by GC-MS", Chemical Analysis and Meterage, 2003, vol. 12, Issue No. 3, pp. 25-26; 6 pgs; Translation in English provided.
Encyclopedia of Chemical Technology, vol. 5, Nov. 1993; 6 pgs; Translation in English provided.
"Manufacture and use of epoxy resin", edited by Shanghai Resin Factory, published by China Petrochemical Press, First Edition, Oct. 1974; 16 pgs; Translation in English provided.
Gilman, Henry, et al—"Organic synthesis", Part 1, published by Scientific Publishing, 1957 (with abstract); 4 pgs.
Handbook of Chemical Products, Heavy Organic Chemicals, Second edition, published by Chemical Industry Press, Jan. 1995; 13 pgs; Translation in English provided.
Kiseleva, R. A., et al—"Study of the Interaction of Dibasic Acids with Glycerol", J. App. Chem. USSR, 1971, vol. 44, pp. 2086-2090; 5 pgs.
Handbook of Corrosion Data and Material Selection, published by Chemical Industry Press, edited by Jingyi Zuo, Yu Zuo; First edition, Oct. 1995, 5 pgs; Translation in English provided.
Handbook of Azeotropic Mixture, edited by Information Department of Comprehensive Scientific Technology Research Institution of Fushun City, 1993; 8 pgs; Translation in English provided.
"Industry Chemical Reaction and Application", published by Chinese Scientific Technology University Press, 1999; 4 pgs; Translation in English provided.
"Epoxy resin", published by Shanghai People's Publishing House, 1971; Translation in English provided; 21 pgs.
Boschan, Robert, et al—"The Role of Neighboring Groups in Replacement Reactions. XXI. Front-side Participation of Acetoxy Group. Catalytic Effect of Acetic Acid on the Reaction of Glycols with Hydrogen Chloride", Journal of the American Chemical Society, 1956, vol. 78, pp. 4921-4925; 5 pgs.
Encyclopedia for Chinese Adult Education, 1994, p. 623; 10 pgs; Translation in English provided.
New Experimental Chemical Course 1, Basic Operation I, Section 4, Separation and Purification, pp. 251-252, Issued Sep. 20, 1975 (with English Translation).
Copyright Mar. 1992, Advanced Organic Chemistry, 4th Ed., pp. 889, 908 and 937.
Yong, K.C., et al., "Refining of Crude Glycerine Recovered from Glycerol Residue by Simple Vacuum Distillation," Journal of Oil Palm Research, vol. 13, No. 2, Dec. 2001, pp. 39-44.
Friedel et Silva, Bulletin de la Société Chimique de Paris, Arnnée 1873, 1er semestre—Nouvelle Serie—Tome XIX, p. 98.
I.S. Neuberg, Biochemische Zeitshrift, 1930, vol. 221, pp. 492-493.
F. Krausz Ann. De Chimie, 12e série, t. 4 Nov.-Dec. 1949, pp. 811-931.
Glycerin : An overview, Soap and Detergent Association. Copyright 1990 by the Soap and Detergent Association.
Chemical and Engineering News, 1948, 26 (38), pp. 2770-2771.
Fairbourn et al., "The Partial Esterification of Polyhydric Alcohols. Part XII. The Function of Ethylene-oxide Rings," J. Chem. Soc. 1932, pp. 1965-1972, Received, Apr. 6, 1932.
Clarke et al., Organic Syntheses, Coll., vol. 1, p. 233, (1941); vol. 3, p. 47, ( 1923).
Braun, Organic Syntheses, Coll., vol. 2, p. 256, (1943); vol. 6, p. 30, (1936).
Conant et al. Organic Syntheses, Coll., vol. 1, p. 292, (1941); vol. 2, p. 29, (1922).
Bull. Soc. Chim. Fr. (1943), 10, pp. 52-58, with English Translation.
Schröder et al. "Glycerol as a By-Product of Biodiesel Production in Diets for Ruminants," Institute of Animal Nutrition, Physiology and Metabolism, University of Kiel, 24098 Kiel.
"Chemical Properties and Derivatives of Glycerol", (1965), published by Glycerine Producers' Association in New York, pp. 1-20.
G.W. Busby and D.E. Gosvenor, "The Purification of Glycerin by Ion-Exchange," The Journal of the American Oil Chemists' Society, vol. 29, No. 8, pp. 318-320 (1952).
L.L. Lamborn, "Modern Soaps, Candles and Glycerin," D. Van NOstrand Company, London, third edition 1918, pp. 542-550, 573-574.
G. Knothe, "Historical perspectives on vegetable oil-based diesel fuels", Inform, vol. 12, Nov. 2001. pp. 1103-1107.
U. Schuchardt et al., "Transesterification of Vegetable Oils: a Review," J. Braz. Chem. Soc., vol. 9, No. 1, 199-210, 1998.
S. Claude, "Research of new outlets for glycerol—recent developemnts in France," Fett/Lipid 101 (1999), Nr. 3, S 101-104.
C.B. Prakash, "A critical review of Biodiesel as a Transportation Fuel in Canada," for the Transportation Systems Branch Air Pollution Prevention Directorate Enviornment Canada, Mar. 25, 1998, pp. 1-104.
H. Fukuda et al., "Biodiesel Fuel Production by transesterification of Oils", Journal of Bioscience and Bioengineering, vol. 92, No. 5, pp. 405-416 (2001).
Medium and Long-term Opportunities and Risks of the Biotechnological Production of Bulk Chemicals from renewable Resources—The Potential of White Technology—The BREW project—Final Report—prepared under the European Commission GRXTH Programme (DG Research) Ulrecht, Sep. 2006 (pp. 29-31).
Ullmann's Encyclopedia Industrial Chemistry, 5th Ed. vol. A6 (1988) pp. 401-477.
Polymer Science Dictionary, M.S.M., Elsevier Applied Chemistry, London & New York, 1989 p. 86.
Perry's Chemical Engineers' Handbook, 6th Edition, Section 21, pp. 21-55.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte—und Wassermengenwirtschaft e; V; -2005 p. 81/-8/5., vol. 5.
Klaus Weissermel, et al., "Industrial Organic Chemistry," (3rd Completely Revised Edition); VCH 1997. p. 93-98.
Klaus Weissermel, et al., "Industrial Organic Chemistry," (3rd Completely Revised Edition); VCH 1997. p. 276-277.
Klaus Weissermel, et al., "Industrial Organic Chemistry," (3rd Completely Revised Edition); VCH 1997. p. 347-355.
Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).
Ying Ling Liu, "Phosphorous-Containing Epoxy Resins from a Novel Synthesis Route," Journal of Applied Polymer Science, vol. 83, 1697-1701 (2002).
M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006) w/ English Abstract.
U.S. Appl. No. 60/734,659, filed Nov. 8, 2005.
U.S. Appl. No. 60/734,627, filed Nov. 8, 2005.
U.S. Appl. No. 60/734,657, filed Nov. 8, 2005.
U.S. Appl. No. 60/734,658, filed Nov. 8, 2005.
U.S. Appl. No. 60/734,635, filed Nov. 8, 2005.
U.S. Appl. No. 60/734,634, filed Nov. 8, 2005.
U.S. Appl. No. 60/734,637, filed Nov. 8, 2005.
U.S. Appl. No. 11/915,046, filed Nov. 20, 2007, Krafft, et al., unpublished.
U.S. Appl. No. 60/734,636, filed Nov. 8, 2005.
U.S. Appl. No. 11/915,088, filed Nov. 20, 2007, Krafft, et al., unpublished.
U.S. Appl. No. 60/560,676, filed Apr. 8, 2004, Gilbeau, et al. et al.
U.S. Appl. No. 61/013,680, filed Dec. 14, 2007, Krafft, et al.
U.S. Appl. No. 61/013,704, filed Dec. 14, 2007, Gilbeau, et al.

U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Boulos, et al.
U.S. Appl. No. 12/600,018, filed Nov. 13, 2009, Borremans.
U.S. Appl. No. 12/663,749, filed Dec. 9, 2009, Krafft, et al.
U.S. Appl. No. 12/663,753, filed Dec. 9, 2009, Krafft, et al.
U.S. Appl. No. 12/663,887, filed Dec. 10, 2009, Krafft, et al.
Herman A. Bruson, et al., "Thermal Decomposition of Glyceryl Carbonates," Journal of the American Chemical Society, vol. 74, Apr. 1952 pp. 2100-2101.
Perry's Chemical Engineers Handbook 7th Ed., 11th Section, 1997, pp. 11.1-11.118 (submitted into two parts).
Perry's Chemical Engineers Handbook 7th Ed., 13th Section, 1997, pp. 13.1-13.108.
Perry's Chemical Engineers Handbook 7th Ed., 15th Section, 1997, pp. 15.1-15.47.
Ullmann's Encyclopedia of Industrial Chemistry 5th Ed., vol. A23, 1993, pp. 635-636.
Ullmann's Encyclopedia of Industrial Chemistry 5th Ed., vol. A13, 1989, p. 289.
Ullmann's Encyclopedia of Industrial Chemistry 5th Ed., vol. A11, 1988, pp. 354-360.
Application No. FR 06.05325 filed Jun. 14, 2006 by Solvay S.A.—priority document to EP2007/55742 published as WO 2007/144335 17 pgs.
Application No. FR 07.53863 filed Mar. 15, 2007 by Solvay S.A. and published as FR2913683, 19 pgs—priority document to EP2007/55742 published as WO2007/144335 29 pgs.
Gibson, "The preparation, properties, and uses of glycerol derivatives, Part III. The Chlorohydrins", 1931, Chemistry and Industry, Chemical Society, pp. 949-975.
Carre et al, 1931, "La transformation des alcools polyatomiques en mono-et en polychlorohydrines au moyen du chlorure de thionyle", Bulletin De La Societe Chimique De France, Societe Francaise De Chimie. Paris—ISSN 0037-8968, vol. 49, No. 49, pp. 1150-1154.
Fauconner, 1888, "Preparation de l'epichlorhydrine", Bull. Soc. Chim. FR, No. 50, pp. 212-214 (with enclosed translation in English).
Ullmann's Encyclopedia of Industrial Chemistry, "Industrially important epoxides", 1987, Fifth Completely Revised Edition, vol. A9, pp. 539-540.
Bonner et al, "The composition of constant boiling hydrochloric acid at pressures of 50 to 1220 millimeters", 1930, Journal of American Chemical Society, vol. 52, pp. 633-635.
Muskof et al, "Epoxy Resins" in Ullmann's Encyclopedia of Industrial Chemistry, 1987, 5th Ed., vol. A9, pp. 547-563.
Novelli, A., "The preparation of mono-and dichlorohydrins of glycerol", 1930, Anales Farmacia Bioquimica, vol. 1, pp. 8-19 (with English abstract).
Derwent Publications, AN 109:6092 CA, JP 62-242638, Oct. 23, 1987, 1 pg.
Derwent Publications, AN 1987-338139 [48], JP 62-242638, Oct. 23, 1987, 1 pg.
I. Miyakawa et al, Nagoya Sangyo Kagaku Kenkyusho Kenkyu Hokoku, 10, 49-52 (1957). (Abstract in English only). 1 pg.
Han Xiu-Ying et al, Shanxi Daxue Xuebao Bianjibu, 2002, 25(4), 379-80. (Abstract in English only), 1 pg.
Semendyaeva et al, 1981. Khimicheskaya Promyshlennost, Seriya: Khomaya Promyshlennost, 5. 21-2 (CA Summary). XP 002465275, 1 pg.
Rudnenko, EV, et al., 1988, Lakokrasochnye Materially i 1kh Primenenie, 4 69-71 (CA Summary) XP 002465276, 1 pg.
Kirk-Othmer Encyclopedia of Chemical Technology, 1978, 3rd Ed., vol. 4, Blood, Coagulants and Anticoagulants to Cardiovascular Agents. p. 847-848.
Jeffrey Lutje Spelberg, et al, A Tandem Enzyme Reaction to Produce Optically Active Halohydrins, Epoxides and Diols, Tetrahedron: Asymmetry, Elsevier Science Publishers, vol. 10, No. 15, 1999, pp. 2863-2870.
Oleoline.com. Glycerine Market report, Sep. 10, 2003, No. 62, 31 pgs.

Notification Under Act. No. 100/2001, Coll. As Amended by Act No. 93/2004, Coll. To the extent of Annex No. 4 (SPOLEK) Nov. 30, 2004, 80 pgs.
Documentation Under Act. No. 100/2001 Coll. As Amended by Act. No. 93/2004 Coll in the scope of appendix No. 4 (SPOLEK) Jan. 11, 2005, 86 pgs.
K. Weissermel & H.J. Arpe, Industrial Organic Chemistry, Third, Completely Revised Edition, VCH, 1997, pp. 149 & 275.
Industrial Bioproducts: "Today and Tomorrow." Energetics, Inc. For the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & Sons, Inc.
Ullmann's Encyclopedia of Industrial Chemistry, Fifth, Completely Revised Edition, 1988, vol. A13, pp. 292-293.
The Merck Index, Eleventh Edition, 1989, pp. 759-760.
Ullmann's Encyclopedia of Industrial Chemistry, Fifth completely Revised Edition, vol. A1, 1985, pp. 427-429.
Ullmann's Encyclopedia of Industrial Chemistry, Fifth Completely Revised Edition, vol. A6, 1986, pp. 240-252.
Hancock, E.G., Propylene and its Industrial Derivatives, 1973, pp. 298-332.
K. Weissermel & H.J. Arpe, Industrial Organic Chemistry, Third, Completely Revised Edition, VCH 1997, pp. 149-163.
K. Weissermel & H.J. Arpe, in Industrial Organic Chemistry, Third, Completely Revised Edition, VCH 1997, pp. 275-276.
Robert T. Morrison & Robert N. Boyd, Organic Chemistry, 5th Ed., vol. II, pp. 666 to 667 and 712 to 714 (Japanese Translation), published on Jul. 10, 1970, Tokyo Kagaku Dozin Co., Ltd. (and copies of similar passages but retrieved from the English Fifth Edition of the Book, 1987).
Perry's Chemical Engineers' Handbook, Sixth Edition, Robert H. Perry, Don Green, 1984, Section 21-64 to 21-68.
Iwanami et al, Dictionary of Physics and Chemistry, Third Edition, Ryo Midorikawa /Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEK) Apr. 2005.
Kirk Othmer Encyclopedia of Chemical Technology, Third Edition, vol. 12, 1980, pp. 1002-1005.
Chemical Engineering Handbook, the 6th Edition, Edited by the Society of Chemical Engineers, published by Maruzen Co, Ltd., 1999, pp. 1296-1306 Pub. Feb. 25, 1999 w/English translation of p. 1296, Table 28.4, p. 1298, left column, lines 4-13 and p. 1305, Table 28.10.
Product Brochure of De Dietrich Company, Apr. 1996, pp. 3, 8 and 9 w/English translation of p. 8, left column, lines 1-4, p. 9.
The Journal of the American Chemical Society, vol. XLV, Jul.-Dec. 1923, pp. 2771-2772.
Berichte Der Deutschen Chemischen Gesellschaft, 1891, vol. 24, pp. 508-510.
Catalogue of Nittetu Chemical Engineering Ltd. (Published in Mar. 1994).
12093 Chemicals, The Chemical Daily Co., Ltd. (Published on Jan. 22, 1993) with attached English translation of relevant excerpts, 24 pgs.
Chemicals Guide, Chemical Daily Co., Ltd. (Published on Jun. 15, 1990) with attached English translation of relevant excerpts.
J.B. Conant, et al, "Glycerol a,y-dichlorohydrin", Organic Syntheses Coll., 1941, vol. 1, p. 292-294 (5 pp.).
Gilman H., Organic Synthesis, Section 1, pp. 234-235 (no date)—attached English translation only.
Industrial Chemical Encyclopedia 5, p. 457 (no date)—attached English translation only.
"Epoxy resins", p. 36-46, by Shangai Resin Plant, Shangai People's Press, 1971—attached English translation only.
Martinetti, R. et al. "Environnement Le Recyclage du l'eau" Industrie Textile, Ste Sippe Sarl, Metz, FR, No. 1300 (Jul. 1, 1998), ISSN: 0019-9176 (no English abstract available)—8 pp.

"Rainwater Harvesting and Utilization" (United Nations Environment Program) Mar. 2002; XP003003726; Internet Citation extracted online on Jan. 1, 2006: URL:http://www.unep.or.ip/letc/Publication—4 pp.

Myszkowski, J. et al. "Removal of chlorinated organic impurities from hydrogen chloride"; English Chemical Abstract summary only of Polish Patent No. 136598 B2 (Mar. 31, 1986); XP002352444; 1 pp.

Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.

Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.

Laine, D.F. et al. "The destruction of organic pollutants under mild reaction conditions; A review" Michochemical Journal, vol. 85, No. 2, 2007 pp. 183-193; available online Aug. 17, 2006; 12 pp.

U.S. Appl. No. 12/681,083, filed Mar. 31, 2010, Bobet, et al.

[Unknown Author], Kirk Othmer Encyclopedia of Chemical Technology—vol. 2, p. 156, John Wiley and Sons, 1992.

Ma Zengxin et al, "recovery of Polyglycerol from residues of Synthetic Glycerol" Riyong Huaxue Gongye, 1997, 4, 21023 (English Abstract only).

Sang Hee Lee et al "Direct preparation of Dichloropropanol (DCP) from Glycerol Using Heteropolyacid (HPA) Catalysts: A Catalyst Screen Study," Catalysis Communications (9), 2008, p. 1920-1923.

Production and Prospect of the World Natural Glycerol by Zhu Shiyong, Cereals and Oils, vol. 1, 1997, pp. 33-38 (No English Translation).

Vinnolit; Vinnolit receives EU grant for water recycling project: Press Release, 2008: http://www vinnolit.de/vinnolit.nsf/id/EN_Vinnolit_receives_EU_grant_for_water_recylcing_project_.

N.W. Ziels, Journal of American Oil Chemists' Society, Nov. 1956, vol. 33, pp. 556-565.

Perry's Chemical Engineers Handbook, Sixth Edition. McGraw Hill: Inc., (1984) Section 18.

vol. 83: Unit Operations of Ullman's Encyclopedia of Industrial Chemistry, Fifth Completely Revised Edition. Published by VCH, 1988.

W. Giger et al., "14C/12C-Rations in Organic Matter and Hydrocarbons from Dated Lake Sediments," Nuclear Instruments and Methods in Physics Research B5 (1984), 394-397. XP-002631954.

Jurgen O. Metzger, "Fats and Oils as Renewable Feedstock for Chemistry," Eur. J. Lipid. Sci. Technol. (2009), 111, 865-876. XP-002631953.

Bruce M. Bell, "Glycerin as a Renewable Feedstock for Epichlorohydrin Production. The GTE Process," Clean-Soil, Air, Water, vol. 36, No. 8, (2006) pp. 657-661. XP-002631952.

U.S. Appl. No. 13/131,516, not yet assigned, Patrick Gilbeau.

U.S. Appl. No. 13/060,421, filed Feb. 23, 2011, Dominique Balthasart et al.

U.S. Appl. No. 13/063,230, filed Mar. 10, 2011, Philippe Krafft et al.

U.S. Appl. No. 12/745,802, Not yet assigned, Patrick Gilbeau, et al.

RD 436093, RD, Aug. 10, 2000, Akzo Nobel, Only Derwent and CAS abstracts in English available.

Ullmann's Encyclopedia of Industrial Chemistry, 2005, "pH Measurement and Control", Wiley-VCH GmbH & Co. KGaA, Weinheim, 10.1002/14356007.e19_e01; pp. 1-31 (32 pgs).

U.S. Appl. No. 12/864,211, filed Jul. 27, 2010, Patrick Gilbeau, et al.

Encyclopedia of Experimental Chemistry I, Basic Operation I, edited by The Chemical Society of Japan, Maruzen Co., Ltd., Nov. 5, 1990, 4th Edition, pp. 161 to 165 and 184 to 191 (no English translation available.

Encyclopedia of Chemistry 3, edited by Editorial Committee of Encyclopedia of Chemistry, Kyoritsu Shuppan Co., Ltd., Sep. 30, 1960, 1st Edition, 1st printing, pp. 312 and 313 (no English translation available).

Clarke et al., Org Synth., Coll. vol. 1, p. 233-234, 1964.

Braun, Org. Synth., Coll., vol. 2, p. 256-259, 1957.

Kirk Othmer Encyclopedia of Chemical Technology, 3rd Edition, vol. 9, pp. 267-289, 1980.

* cited by examiner

I.

II.

III.

IV.

V.

XIII.

PRODUCT CONTAINING EPICHLOROHYDRIN, ITS PREPARATION AND ITS USE IN VARIOUS APPLICATIONS

CROSS-REFERENCE TO RELATED APPLICATIONS

The present patent application is a U.S. national stage application under 35 U.S.C. §371 of International Application No. PCT/EP2008/057246 filed Jun. 11, 2008, which claims the benefit of the U.S. Provisional patent application No. 61/007,661 filed on Dec. 14, 2007, of the French Patent applications No. FR 07/55696 filed on Jun. 12, 2007, No. FR 07/57751 filed on Sep. 21, 2007, and of the U.S. Provisional Patent Application No. 61/013,672 filed on Dec. 14, 2007, the content of all of these applications being incorporated herein by reference for all purposes.

The present invention relates to an epichlorohydrin-based product, to a process for its preparation and to the use of the product in various applications.

Epichlorohydrin is a reaction intermediate in the manufacture of various products like for instance epoxy resins, synthetic elastomers, glycidyl ethers, polyamide resins, etc. (Ullmann's Encyclopedia of Industrial Chemistry, Fifth Edition, Vol. A9, p. 539).

Epichlorohydrin can be obtained by several routes, like for instance, epoxidation of allyl chloride with hydrogen peroxide or dehydrochlorination of dichloropropanol.

The dichloropropanol route presents the advantage that dichloropropanol can be obtained by hydrochlorination of glycerol. This glycerol can be obtained from fossil raw materials or from renewable raw materials, e.g., from fats or oils of animal or plant origin by transesterification processes.

In some cases the epichlorohydrin thus obtained is contaminated with impurities which render them unsuitable for certain applications.

The goal of the invention is to solve those problems by providing a new product containing epichlorohydrin suitable in all known applications.

The invention therefore relates in a first embodiment to a product containing epichlorohydrin and at least one alkyl glycidyl ether in an amount of less than 0.1 g/kg of product.

One of the essential characteristics of the present invention resides in the identification of unwanted impurities. Glycidyl alkyl ethers have indeed been identified as unwanted impurities. They are very difficult to separate from epichlorohydrin because of similar boiling points. The presence of glycidyl alkyl ethers in epichlorohydrin may prove troublesome in some of these applications for various reasons. Glycidyl ethers are suspected to have reproductive toxicity, immunotoxicity and toxicity to the skin. Glycidyl methyl ether is also suspected to be mutagenic. Those ethers can interfere in the synthesis processes as the molecules could be inserted for example in a polymeric chain through the opening of the epoxide ring. They can remain in the final products and possibly degrade with a concomitant deterioration of the properties of the final products. They can exhibit or degrade in compounds exhibiting some toxicity leading to safety issues especially when the final products are intended to be in contact with food and drink. Moreover, they can accumulate in and contaminate industrial waters such as wastewaters for instance or water containing pulp that is recycled in the pulp and paper industry. In the latter case, their higher concentration can increase contamination of the paper made using the recycled water.

The content of alkyl glycidyl ether, in the product of the invention is preferably lower than or equal to 0.08 g/kg, more preferably lower than or equal to 0.06 g/kg, still more preferably lower than or equal to 0.04 g/kg, yet preferably lower than or equal to 0.020 g/kg, most preferably lower than or equal to 0.01 g/kg and particularly most preferably lower than or equal to 0.005 g/kg. This content is usually higher than or equal to 0.0005 g/kg.

The product according to the invention has an epichlorohydrin content which is generally higher than or equal to 900 g/kg of product, preferably higher than or equal to 950 g/kg, more preferably higher than or equal to 990 g/kg, yet more preferably higher than or equal to 999 g/kg and most preferably higher than 999.5 g/kg.

The alkyl group of the alkyl glycidyl ether can be a linear or branched or alicyclic aliphatic alkyl group and is preferably a linear or branched aliphatic group.

The alkyl group of the alkyl glycidyl ether contains a number of carbon atoms which is generally higher than or equal to 1, often higher than or equal to 2 and frequently higher than or equal to 3. That number of carbon atoms is generally lower than or equal to 10, often lower than or equal to 8 and frequently lower than or equal to 6.

The alkyl group is preferably selected from the methyl, ethyl, propyl, butyl, pentyl, hexyl, heptyl and octyl groups and more preferably from the methyl, ethyl, propyl and butyl groups and particularly preferably from the methyl and ethyl groups. Very particularly preferably, the alkyl group is a methyl group. The propyl group can be chosen from the n-propyl and isopropyl groups and is preferably an isopropyl group. The butyl group can be chosen from the 1-butyl, 2-butyl, isobutyl and tert-butyl groups, preferably from the isobutyl and tert-butyl groups.

The product according to the invention may contain in addition to alkyl glycidyl ether and epichlorohydrin, at least one halogenated hydrocarbon. The halogenated hydrocarbon may be an aliphatic or an aromatic halogenated hydrocarbon, optionally containing oxygen. It is often an aliphatic halogenated hydrocarbon and frequently an aromatic hydrocarbon.

The content of the halogenated hydrocarbon in the product is usually of less than 1 g/kg of product, preferably less than or equal to 0.8 g/kg of product, preferably less than or equal to 0.6 g/kg, more preferably less than or equal to 0.5 g/kg, yet more preferably less than or equal to 0.4 g/kg, still more preferably less than or equal to 0.2 g/kg, most preferably less than or equal to 0.1 g/kg, yet most preferably less than or equal to 0.05 g/kg, still most preferably less than or equal to 0.01 g/kg, and most particularly preferably less than or equal to 0.001 g/kg. This content is generally greater than or equal to 0.001 mg/kg.

That halogenated hydrocarbon can be chosen from chloropropene, trichloropropene, trichloropropane, chloropropanol, chloropropenol, dichloropropene, dichloropropane, dichloropropanol, monochloropropanediol, chloroethers, monochlorobenzene, and any mixture of at least two of them.

The halogenated hydrocarbon can be chosen from aliphatic halogenated hydrocarbons such as chloropropene, often 2-chloro-1-propene, frequently 1-chloro-1-propene cis, usually 1-chloro-1-propene trans and specifically 3-chloro-1-propene, and any mixture of at least two of them chloropropane, often 2-chloropropane, frequently 1-chloropropane, and any mixture of at least two of them chloromethane, often dichloromethane, frequently trichloromethane, usually tetrachloromethane and any mixture of at least two of them dichloroethane, often 1,2-dichloroethane,
chloroethanol, often 2-chloroethanol,
trichloropropene, often 1,3,3-trichloro-1-propene-cis, frequently 1,3,3-trichloro-1-propene-trans, usually 1,2,3-trichloropropene-cis (?), specifically 1,2,3-trichloropropene-transand any mixture of at least two of them
trichloropropane, often-1,2,3-trichloropropane, frequently 1,1,1-trichloropropane, usually 1,1,3-trichloropropane, commonly 1,1,2-trichloropropane and any mixtures of at least two of them.
chloropropanol, often 3-chloro-1-propanol,
chloropropenol, often 2-chloro-2-propen-1-ol, frequently 3-chloro-2-propene-1-ol cis and specifically 3-chloro-2-propene-1-ol trans, and any mixture of at least two of them
dichloropropene, often cis-1,3-dichloropropene, frequently trans-1,3-dichloropropene, usually 3,3-dichloro-1-propene, frequently 2,3-dichloro-1-propene, usually 1,3-dichloro-1-propene-cis, specifically 1,3-dichloro-1-propene-trans, and any mixture of at least two of them,
dichloropropane, preferably 1,3-dichloropropane, 1,2-dichloropropane, 2,2-dichloropropane, and any mixture of at least two of them
dichloropropanol, often-1,3-dichloropropan-2-ol, 2,3-dichloropropan-1-ol, and mixtures thereof,
monochloropropanediol, often 3-chloro-1,2-propanediol, frequently 2-chloro-1,3-propanediol, and mixtures thereof, and
chloroethers, preferably chosen from chloroethers of crude formula: $C_6H_{10}Cl_2O_2$, $C_6H_{12}Cl_2O$, $C_6H_9Cl_3O_2$, $C_6H_{11}Cl_3O_2$, and mixtures of at least two of them, compounds of crude formula $C_4H_7ClO_2$, $C_6H_9Cl_3$, $C_6H_9Cl_3O_2$, $C_9H_{17}Cl_3O_4$, $C_9H_{15}Cl_5O$, $C_3H_3Cl_3$, and mixtures of at least two of them dichloroepoxypropane, and any mixture of at least two of them.

Aromatic halogenated hydrocarbons comprise at least one ring of aromatic nature and a halogen atom. The halogen atom is preferably directly attached to the aromatic ring. The halogen may be chosen from fluorine, chlorine, bromine, iodine and mixtures thereof. Chlorine is preferred. The aromatic ring may be mononuclear or polynuclear, and is preferably mononuclear. The aromatic halogenated hydrocarbons may be chosen from mono-, di-, tri-, tetra-, penta- and hexachloro-benzenes and/or naphthalenes. Monochlorobenzene is particularly preferred.

Without wishing to be tied to one theoretical explanation, it is believed that monochlorobenzene may come from the process for manufacturing epichlorohydrin, in particular when this is obtained by dehydrochlorination of dichloropropanol. More specifically, it is believed that monochlorobenzene may be present in the dichloropropanol, in particular when this is obtained by a process for chlorinating glycerol using a chlorinating agent containing hydrogen chloride. More specifically still, it is believed that chlorobenzene may be present in the hydrogen chloride, in particular when this comes from another manufacturing process, such as the manufacture of isocyanates, diisocyanates or polyisocyanates, such as for example 4,4-methylenediphenyl diisocyanate (MDI) or toluene diisocyanate (TDI) or hexamethylene-1,6-diisocyanate (HDI).

The product according to the invention can contain chloropropene, in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg. That content is usually of at least 0.001 mg/kg. The chloropropene may be selected from 2-chloro-1-propene, 1-chloro-1-propene cis, 1-chloro-1-propene trans, 3-chloro-1-propene, and any mixture of at least two of them.

The product according to the invention can contain trichloropropane, in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg, in an amount of commonly less than or equal to 0.008 g/kg of product, more commonly of less than or equal to 0.006 g/kg, yet more often of less than or equal to 0.004 g/kg, still more often of less than or equal to 0.002 g/kg, most frequently of less than or equal to 0.001 g/kg, yet most frequently of less than or equal to 0.0005 g/kg. That content is usually of at least 0.001 mg/kg.

The product according to the invention can contain trichloropropene, in an amount a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg. That content is usually of at least 0.001 mg/kg. This content is at least 0.001 g/kg. The trichloropropene may be selected from 1,3,3-trichloro-1-propene-cis, 1,3,3-trichloro-1-propene-trans, 1,2,3-trichloropropene-cis, specifically 1,2,3-trichloropropene-trans and any mixtures of at least two of them.

The product according to the invention can contain chloropropenol, in a content a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg. That content is usually of at least 0.001 mg/kg. The chloropropenol may be selected from 2-chloro-2-propen-1-ol, 3-chloro-2-propene-1-ol cis, 3-chloro-2-propene-1-ol trans and any mixtures of at least two of them.

The product according to the invention may contain dichloropropene, in a content a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg. That content is usually of at least 0.001 mg/kg. The dichloropropene may be selected from 3,3-dichloro-1-propene, 2,3-dichloro-1-propene, 1,3-dichloro-1-propene-cis, 1,3-dichloro-1-propene-trans, and any mixtures of at least two of them.

The product according to the invention can contain dichloropropane, in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.2 g/kg, yet more frequently less than or equal to 0.05 g/kg, still more often less than or equal to 0.01 g/kg, and in particular less than or equal to 0.001 g/kg. That content is usually of at least 0.001 mg/kg . . . . The dichloropropane may be selected from 1,3-dichloropropane, 1,2-dichloropropane, 2,2-dichloropropane, and any mixture of at least two of them.

The product according to the invention can contain dichloropropanol, in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg. That content is usually of at least 0.001 mg/kg. The dichloropropanol may be selected from 1,3-dichloropropan-2-ol, 2,3-dichloropropan-1-ol and any mixtures thereof.

The product according to the invention can contain monochloropropanediol, in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg. That content is usually of at least 0.001 mg/kg. The monochloropropanediol may be selected from 3-chloro-1,2-propanediol, 2-chloro-1,3-propanediol and any mixtures thereof.

The product according to the invention usually can contain chloroethers in in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg. That content is usually of at least 0.001 mg/kg. The chloroethers may be selected from chloroethers of crude formula $C_6H_{10}Cl_2O_2$, $C_6H_{12}Cl_2O$, $C_6H_9Cl_3O_2$, $C_6H_{11}Cl_3O_2$, and any mixtures thereof.

The product according to the invention usually contains chlorobenzene, often monochlorobenzene, in an amount in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg. That content is usually of at least 0.001 mg/kg.

The product according to the invention may also contain in addition to epichlorohydrin, alkyl glycidyl ethers and halogenated hydrocarbons, compounds such as for example:
- aldehydes, like acetaldehyde, acrolein, isobutanal, isopentanal, and any mixture of at least two of them,
- ketones, like acetone, chloroacetone, cyclopentanone, 2-butanone, cyclohexanone, 2-methyl-2-cyclopentene-1-one, 3,5-dimethyl-2-cyclohexene-1-one ketone of crude formula $C_5H_{10}O$, $C_6H_{12}O$, and any mixture of at least two of them,
- aliphatic alcohols, like isopropanol, allyl alcohol, glycerol, and any mixture of at least two of them,
- aromatic alcohols like phenol,
- hydroxyketones like hydroxyacetone,
- epoxides different from epichlorohydrin, like propylene oxide, 1,2-epoxyhexane, glycidol, and any mixture of at least two of them
- hydrocarbons like methylcyclopentane, ethylbenzene, and any mixture of at least two of them
- compounds of crude formula $C_6H_{10}O$, $C_7H_{10}O$, $C_7H_{14}O_2$, $C_6H_8O_2$, $C_9H_{10}O_2$, and any mixture of at least two of them.

The product according to the invention can contain at least one aldehyde, in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg. That content is usually of at least 0.001 mg/kg. The aldehyde may be selected from acetaldehyde, acrolein, isobutanal, isopentanal and any mixtures of at least two of them.

The product according to the invention usually can contain acrolein in an amount usually of less than 0.07 g/kg of product, preferably at most 0.01 g/kg and more preferably at most 0.005 g/kg. This content is at least 0.001 g/kg.

The product according to the invention can contain ketones, in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg. That content is usually of at least 0.001 mg/kg. The ketones may be selected from acetone, chloroacetone, 2-butanone, cyclopentanone, cyclohexanone, 2-methyl-2-cyclopentene-1-one, 3,5-dimethyl-2-cyclohexene-1-one, ketones of crude formula $C_5H_{10}O$, $C_6H_{12}O$, and any mixtures of at least two of them.

The product according to the invention can contain cyclopentanone in an amount usually higher than or equal to 0.001 mg/kg, often higher than or equal to 0.01 mg/kg, frequently higher than or equal to 0.1 mg/kg and in particular higher than or equal to 0.001 g/kg. That content is usually lower than or equal to 0.5 g/kg, often lower than or equal to 0.3 g/kg, frequently lower than or equal to 0.1 g/kg, more often lower than or equal to 0.05 g/kg, more frequently lower than or equal to 0.01 g/kg and particularly lower than or equal to 0.005 g/kg. That content is usually higher than or equal to 0.001 mg/kg, often higher than or equal to 0.01 mg/kg, frequently higher than or equal to 0.1 mg/kg, more often higher than or equal to 0.5 mg/kg and in particular higher than or equal to 1 mg/kg The product according to the invention can contain chloroacetone in an amount usually of less than 0.05 g/kg of product, preferably at most 0.03 g/kg and more preferably at most 0.01 g/kg. This content is at least 0.001 g/kg The product according to the invention can contain aliphatic alcohols, in a content usually in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.1 g/kg, yet more frequently less than or equal to 0.05 g/kg, still more often less than or equal to 0.01 g/kg, and in particular less than or equal to 0.001 g/kg. That content is usually of at least 0.001 mg/kg. The aliphatic alcohols may be selected from isopropanol, allyl alcohol, glycerol, and any mixtures of at least two of them.

The product according to the invention can contain hydroxyketones, in a content in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.2 g/kg, yet more frequently less than or equal to 0.05 g/kg, still more often less than or equal to 0.01 g/kg, and in particular less than or equal to 0.001 g/kg. That content is usually of at least 0.001 mg/kg. The hydroxyketone is often hydroxyacetone.

The product according to the invention can contain epoxides different from epichlorohydrin, in a content in a content usually less than or equal to 0.8 g/kg of product, often less than or equal to 0.6 g/kg, frequently less than or equal to 0.5 g/kg, more often less than or equal to 0.4 g/kg, more frequently less than or equal to 0.2 g/kg, yet more often less than or equal to 0.2 g/kg, yet more frequently less than or equal to 0.05 g/kg, still more often less than or equal to 0.01 g/kg, and in particular less than or equal to 0.001 g/kg. That content is usually of at least 0.001 mg/kg. The epoxide may be selected from propylene oxide, 1,2-epoxyhexane, glycidol, and any mixtures of at least two of them.

The product according to the invention can contain glycidol in an amount in a content usually of at most 0.5 g/kg of product, generally of at most 0.2 g/kg, frequently of at most 0.10 g/kg of product, commonly of at most 0.05 g/kg of product, often of at most 0.01 g/kg and frequently of at most 0.005 g/kg.

The product according to the invention usually contains glycerol, hydroxyacetone and glycidol, of which the sum of the contents is less than 0.1 g/kg of product, preferably at most 0.01 g/kg and more preferably at most 0.005 g/kg. This content is at least 0.001 g/kg.

The product according to the invention can be obtained by dehydrochlorination of a composition containing dichloropropanol and at least one chloro alkoxy propanol in an amount usually of less than or equal to 0.1 g/kg of composition.

The alkoxy group of the chloro alkoxy propanol contains a number of carbon atoms which is generally higher than or equal to 1, often higher than or equal to 2 and frequently higher than or equal to 3. That number of carbon atoms is generally lower than or equal to 10, often lower than or equal to 8 and frequently lower than or equal to 6.

The alkoxy group of the chloro alkoxy propanol can be a linear or branched or alicyclic aliphatic alkoxy group and is preferably a linear or branched aliphatic group. The alkoxy group is preferably selected from the methoxy, ethoxy, propoxy, butoxy, pentoxyl, hexoxy, heptoxy and octoxy groups and more preferably from the methoxy, ethoxy, propoxyl and butoxy groups and particularly preferably from the methoxy and ethoxy groups. Very particularly preferably, the alkoxy group is a methoxy group. The propoxy group can be chosen from the n-propoxy and isopropoxy groups and is preferably an isopropoxy group. The butoxy group can be chosen from the 1-butoxy, 2-butoxy, isobutoxy and tert-butoxy groups, preferably from the isobutoxy and tert-butoxy groups.

Preferably the alkyl group of the alkyl glycidyl ether is a methyl group and the alkoxy group of the chloro alkoxy propanol is a methoxy group.

The product according to the invention can be obtained from a composition containing dichloropropanol wherein the content of chloro alkoxy propanol, preferably chloro methoxy propanol is preferably lower than or equal to 0.08 g/kg, more preferably lower than or equal to 0.06 g/kg, still more preferably lower than or equal to 0.04 g/kg, yet preferably lower than or equal to 0.05 g/kg, most preferably lower than or equal to 0.01 g/kg and particularly most preferably lower than or equal to 0.005 g/kg. This content is usually higher than or equal to 0.0005 g/kg.

The chloro methoxy propanol can be selected from 2-chloro-3-methoxy-propane-1-ol, 1-chloro-3-methoxy-propane-2-ol and mixtures thereof.

Without being bound by any theory, it is believed that, when the dichloropropanol is contaminated by various isomers of chloroalkoxypropanol, the dehydrochlorination of dichloropropanol into epichlorohydrin is accompanied by the dehydrochlorination of chloro alkoxy propanol into alkyl glycidyl ethers. Those alkyl glycidyl ethers exhibit usually boiling points very close to that of epichlorohydrin and are, for this reason, very difficult to separate from it.

The chloro alkoxy propanols can be produced during the manufacture of dichloropropanol, especially when the dichloropropanol is obtained by hydrochlorination of a compound containing glycerol and at least one alkyl ether of glycerol. The glycerol alkyl ethers can originate in the process for manufacturing glycerol especially when glycerol is obtained from trans esterification of oils and/or fats of animal and/or plant origin.

The composition containing dichloropropanol according to the invention can be obtained by hydrochlorination of a compound containing glycerol and at least one glycerol alkyl ether in an amount that is usually lower than or equal to 0.6 g/kg, preferably lower than or equal to 0.1 g/kg, more preferably lower than or equal to 0.02 g/kg, yet preferably lower than or equal to 0.015 g/kg and most preferably lower than or equal to 0.01 g/kg. This content is usually higher than or equal to 0.0005 g/kg of compound. The alkyl group in the glycerol alkyl ether is as defined above and is preferably a methyl group.

The invention relates, in a second embodiment, to a process for obtaining a product containing epichlorohydrin and at least one alkyl glycidyl ether in an amount of less than 0.1 g/kg of product. The product can be obtained by dehydrochlorination of a composition containing dichloropropanol and at least one chloro alkoxy propanol in an amount usually of less than or equal to 0.1 g/kg of composition. The composition containing dichloropropanol and at least one chloro alkoxy propanol can be obtained by hydrochlorination of a compound containing glycerol and at least one glycerol alkyl ether in an amount of less than or equal to 0.6 g/kg of compound.

The process for producing the product according to the invention comprises the following steps:

(a) a compound containing glycerol and at least one glycerol alkyl ether in an amount of less than or equal to 0.6 g/kg of compound is reacted with hydrogen chloride in the presence of a carboxylic acid, in order to obtain a composition containing dichloropropanol and at least one chloro alkoxy propanol in an amount of less than or equal to 0.1 g/kg of composition (b) the composition containing dichloropropanol obtained in step (a) is further reacted with a basic agent in order to obtain a product containing epichlorohydrin and at least one alkyl glycidyl ether in an amount of less than 0.1 g/kg of product.

The process comprises optionally the following steps:

(c) a vegetable fat or oil is reacted with an alcohol to obtain the compound containing glycerol, under such conditions that ethers of glycerol are formed and are not separated from glycerol, (d) the compound containing glycerol obtained in step (c) is further subjected to at least one treatment, optionally under reduced pressure, of evaporative concentration, of evaporative crystallization, of distillation, of fractional distillation, of stripping or of liquid-liquid extraction, in order to obtain a compound containing glycerol and at least one glycerol alkyl ether in an amount that is preferably lower than or equal to 0.6 g/kg.

The conditions of step (a) of the process are such as described in the patent application PCT/EP2007/055742 filed in the name of SOLVAY SA, the content of which is incorporated herein by reference, more specifically the passages from page 18, lines 17 to 25, and page 19, line 4 to 19.

The conditions of step (a) of the process are such as described in the patent application PCT/EP2007/055742 filed in the name of SOLVAY SA, the content of which is incorporated herein by reference, more specifically the passages from page 11, line 12, to page 17, line 24, and page 17, lines 31 to 35. The catalyst can be based on dodecanoic acid.

The conditions of steps (c) and (d) of the process are such as described in the patent application PCT/EP2007/055742 filed in the name of SOLVAY SA, the content of which is incorporated herein by reference, more specifically the passages from page 6, line 18, to page 11, line 11.

The invention also relates, in a third embodiment, to the use of the product of the invention described above containing epichlorohydrin and at least one alkyl glycidyl ether in an amount of less than or equal to 0.1 g/kg of product, in the manufacture of epoxy derivatives such epoxy resins, of products which will be used in food and drink applications, of cationization agents, of flame retardants, of products which will be used as detergent ingredients, and of epichlorohydrin elastomers.

1. EPOXY DERIVATIVES 1.1. General

Epoxy derivatives are for example, epoxy resins, glycidyl ethers, glycidyl esters and glycidyl amides and imides. Examples of glycidyl esters are glycidyl acrylate and glycidyl methacrylate.

By epoxy resin, one intends to denote a polymer, the chemical formula of which contains at least one oxirane group, preferably one 2,3-epoxypropyloxy group.

By polymer, one intends to denote molecules with many units joined to each other through chemical covalent bonds, often in a repeating manner, those units being referred as repeat units. The number of repeat units is higher than zero. A polymer contains at least one type of repeat units. When the polymer conatins only one type of repeat units, it is called a homopolymer. When the polymer contains more than one type of repeat units, it is called a copolymer. The copolymers can be of the random type, of the alternating type or of the block type, such as described in "Polymer Science Dictionary, M. S. M., Elsevier Applied Science, London and New York 1989, page 86".

Figure 1:
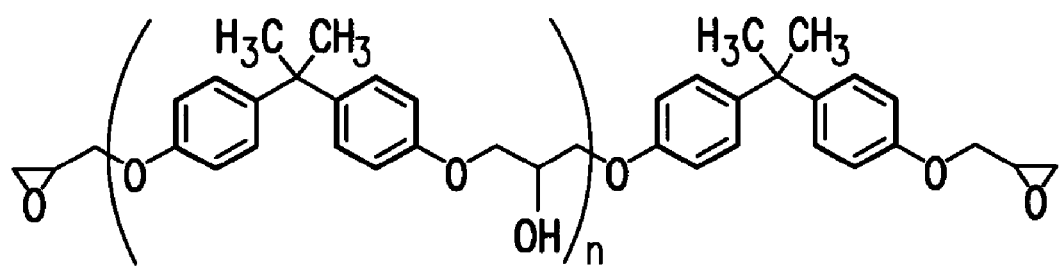
FIG. 1: examples of chemical formula of epoxy resins
Figure 1:
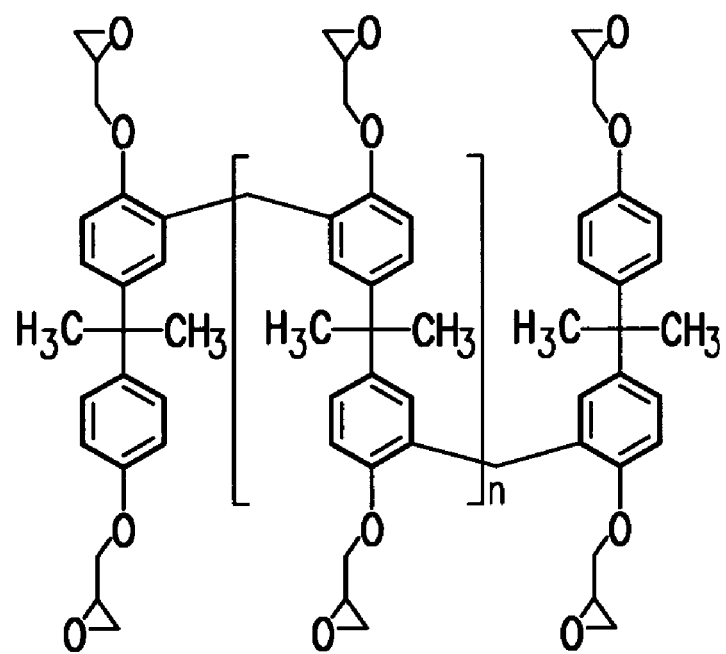

Examples of chemical formulas of epoxy resins are presented in FIG. 1, where n is not zero.

By glycidyl ether, one intends to denote an ether, the chemical formula of which contains at least one glycidyl (2,3-epoxypropyl) group and which is not a polymer. Examples of glycidyl ethers are N-butyl glycidyl ether, $C_{12}$-$C_{14}$ aliphatic glycidyl ethers, o-Cresol glycidyl ether, neopentylglycol diglycidyl ether and butanediol diglycidyl ether.

By glycidyl ester, one intends to denote an ester, the chemical formula of which contains at least one glycidyl (2,3-epoxypropyl) group and which is not a polymer. Examples of glycidyl ester are diglycidyl ester of hexahydrophthalic acid, glycidyl ester of neodecanoic acid, glycidyl acrylate and glycidyl methacrylate.

By glycidyl amides and imides, one intends to denote an amide or an imide, the chemical formula of which contains at least one glycidyl (2,3-epoxypropyl) group and which is not a polymer. Examples of glycidyl amide and imide 1,3,5-tris (2,3-epoxypropyl)-1,3,5-perhydrotriazine-2,4,6-trione and 5,5-dimethyl-1,3-bis(2,3-epoxypropyl)-2,4-imidazolidinedione.

1.2. Co-Reactants

When, the product containing epichlorohydrin according to the invention is used in the manufacture of epoxy derivatives, the product containing epichlorohydrin is usually subjected to a reaction with at least one compound containing at least one active hydrogen atom, preferably at least two active hydrogen atoms, followed by dehydrochlorination as described in Ullmann's Encyclopedia of Industrial Chemistry, 5th Edition, 1987, Vol. A9, pp. 547-553).

The compound containing one active hydrogen atom can be selected from mono alcohol, preferably from 1-butanol, a $C_{12}$ to $C_{14}$ primary alcohol or a cresol, and mixtures thereof, mono carboxylic acids, like for instance neodecanoic acid, acrylic acid, methacrylic acid, or mixtures thereof.

The compound containing at least two active hydrogen atoms can be selected from polyols, polyamines, amino alcohols, polyimides and amides, polycarboxylic acids, and mixtures thereof.

The polyols can be aromatic or aliphatic. Aromatic polyols are preferred.

Preferred aliphatic polyols are aliphatic diols, more preferably selected from butanediol, neopentyl glycol, hydrogenated Bisphenol A (4,4'-dihydroxy-2,2-dicyclohexylpropane), and aliphatic triols, preferably glycerol, poly (oxypropylene)glycol, and mixtures thereof.

Aromatic polyols can be selected from polyhydroxy benzenes, polyphenolic compounds, and mixtures thereof.

Poly hydroxybenzenes are preferably selected from dihydroxy benzenes, trihydroxy benzene, and mixtures thereof. Dihydroxy benzenes are more preferably selected from 1,2-, 1,3-, 1,4-dihydroxy benzenes and mixture thereof.

Trihydroxy benzene is preferably 1,3,5-trihydroxy benzene.

Polyphenolic compounds are generally compounds the molecule of which contains at least one aromatic hydroxyl group.

Suitable compounds having at least one aromatic hydroxyl group which can be employed herein are such as described in U.S. Pat. No. 4,499,255, the content of which is incorporated herein by reference and include, for example, phenols, bisphenols, novolac resins, polyvinyl phenols, the corresponding amine compounds and the like, such as those represented by the formulas I to V of FIG. 2 wherein, each A is independently a divalent hydrocarbon group having from 1 to about 12, preferably from 1 to about 6 carbon atoms, —O—, —S—, —S—S—, —(S=O)$_2$—, —(S=O)— or —(C=O)—, A' is a trivalent hydrocarbon group having from 1 to about 12, preferably from 1 to about 6, carbon atoms; each R is independently hydrogen, a hydrocarbyl group having from 1 to about 10, preferably from 1 to about 4, carbon atoms, a halogen atom, preferably chlorine or bromine or a hydroxyl group or an amino group; each Z is independently —OH or NH2; p has a value of from about 1 to about 100, preferably from about 2 to about 50; m has a value from about 1.00 to about 6 and n has a value of zero or 1.

Figure 2:
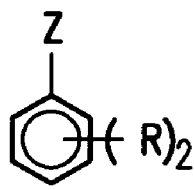
FIG. 2: examples of chemical formula of compounds having at least one aromatic hydroxyl group
Figure 2:
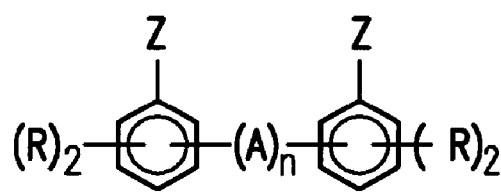
Figure 2:
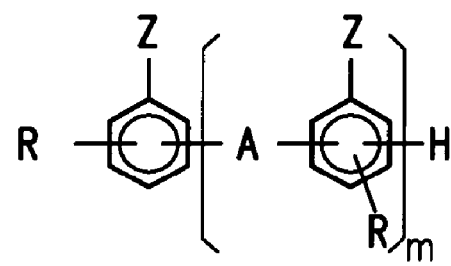
Figure 2:
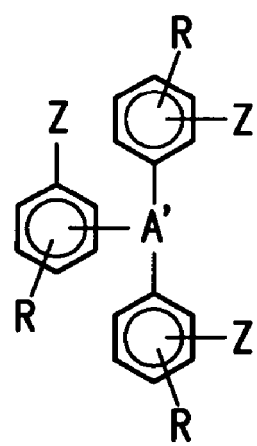
Figure 2:
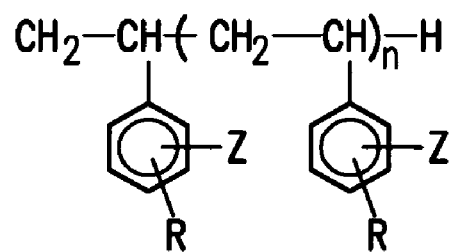
Figure 3:
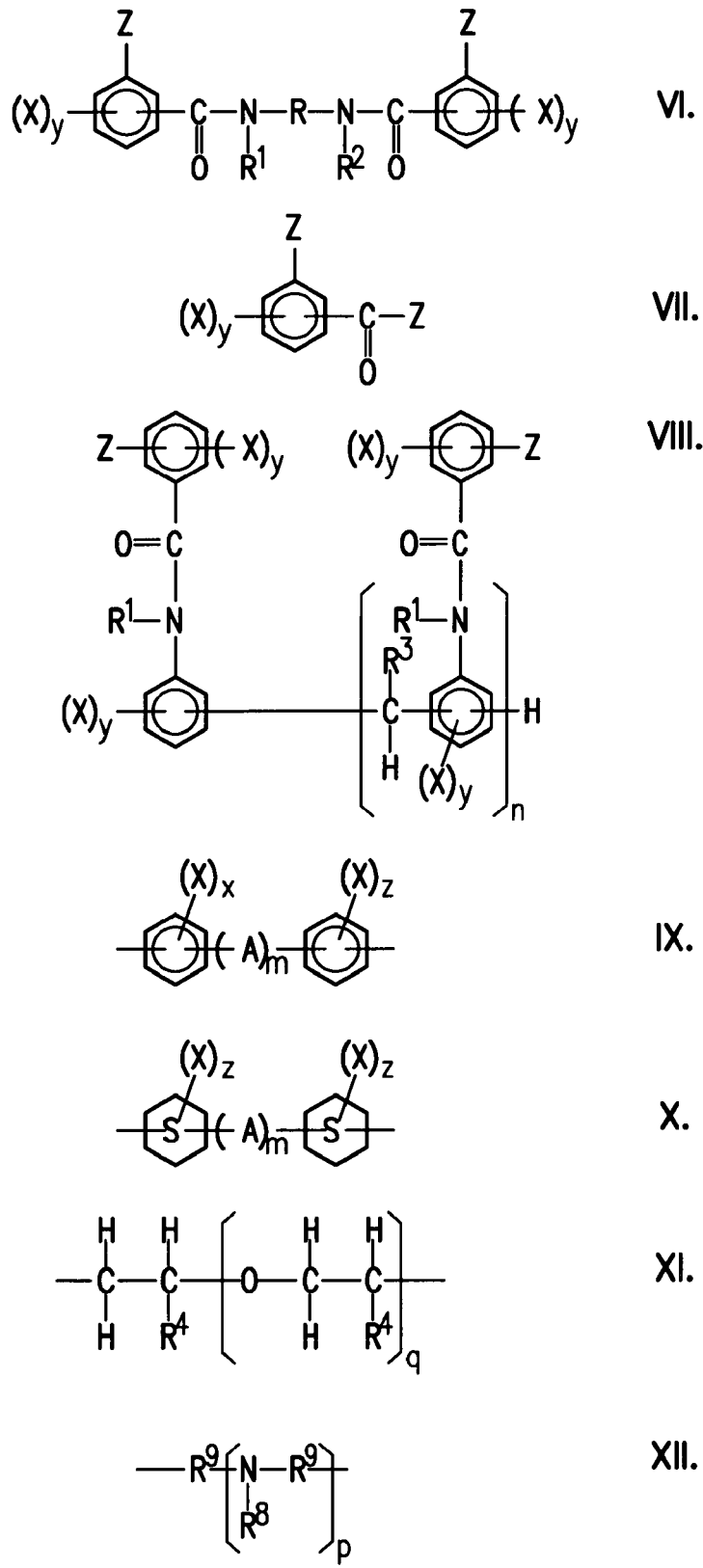
FIG. 3: examples of chemical formula of compounds having at least one aromatic hydroxyl or aromatic amine group per molecule

Also suitable as compounds having at least one aromatic hydroxyl or aromatic amine group per molecule are those represented by the formulas VI to VIII of FIG. 3, wherein each R is a divalent hydrocarbyl group having from 1 to about 18, preferably from about 2 to about 12 and most preferably from about 2 to about 6 carbon atoms, a group represented by the formulas IX, X, XI or XII of FIG. 2, or R can combine with $R^1$ so as to form a stable heterocyclic ring with the nitrogen atoms; each A is independently a divalent hydrocarbyl group having from 1 to about 10, preferably from 1 to about four carbon atoms, —O—, —S—, —S—S—, —(S=O)$_2$—, —(S=O)— or —(C=O)—, each $R^1$ is independently hydrogen, a 2,3-epoxypropyl group, a 2-alkyl-2,3-epoxypropyl group, a monovalent hydrocarbyl group or a hydroxyl substituted monovalent hydrocarbyl group, said hydrocarbyl groups having from 1 to about 9 carbon atoms, said alkyl having from 1 to about 4, preferably 1 to about 3 carbon atoms; each $R^2$ is independently hydrogen or an alkyl group having from 1 to about 4, preferably 1 to about 3 carbon atoms; each $R^3$ is independently hydrogen or an alkyl group having from 1 to about 4 carbon atoms; each $R^4$ is independently hydrogen, a hydrocarbyl or halogen substituted hydrocarbyl group having from 1 to about 9, preferably 1 to about 2 carbon atoms; each $R^8$ is independently selected from the group represented by formula XIV or the same groups as R' except that $R^8$ cannot be a hydrogen; each $R^9$ is independently a divalent hydrocarbyl group having from 2 to about 4, preferably 2 carbon atoms; each Z is independently —OH or —NH2; each X is independently hydrogen, chlorine, bromine or a hydrocarbyl or a hydrocarbyloxy group having from 1 to about 9, preferably 1 to about 6 carbon atoms; each m independently has a value of zero or 1; n has an average value of from about 0.01 to about 6, preferably 0.1 to about 4; p has an average value of from 1 to about 10, preferably from 1 to about 3; q has an average value of at least 1, preferably from 1 to about 150, most preferably from 1 to about 100 and usually from 1 to about 10 and each y and z independently has a value of 1 or 2.

Figure 4:
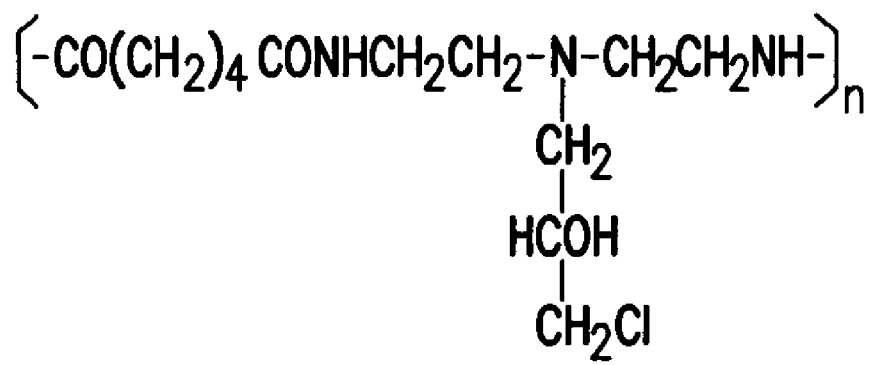
FIG. 4: examples of chemical formula of polycyclopentadiene polyphenols or aromatic polyamines

Also suitable are polycyclopentadiene polyphenols or aromatic polyamines represented by the formula XIII of FIG. 4, wherein Z is —OH or —NH2 and n has a value from 1 to about 5; n' has a value of from about 1 to about 10, preferably from 3 to about 6; each R is independently hydrogen, a hydrocarbyl group having from 1 to about 10, preferably from 1 to about 4 carbon atoms, a halogen atom, preferably chlorine or bromine or a hydroxyl group or an amino group.

Suitable such polycyclopentadiene polyphenols and methods for their preparation can be found in U.S. Pat. No. 4,390,680 issued to Donald L. Nelson on Jun. 28, 1983 which is incorporated herein by reference. The polycyclo-pentadiene aromatic polyamines can be prepared in a similar manner by substituting an aromatic amine for the phenolic compound.

Also suitable are compounds containing both at least one aromatic hydroxyl group and at least one aromatic amine group such as, for example, hydroxy aniline, aminoxylenol and the like.

The polyphenolic compound is preferably selected from Bisphenol A (4,4'-dihydroxy-2,2-diphenylpropane, 4,4'-isopropylidenediphenol), tetrabromo Bisphenol A (4,4'-isopropylidenebis(2,6-dibromophenol)), Bisphenol AF (4,4'-[2,2, 2-trifluoro-1-(trifluoromethypethylidene]bisphenol)=hexafluorobisphenol A (4,4'-dihydroxy-2,2-diphenyl-1,1,1,3,3,3-hexafluoropropane), 1,1,2,2-tetra(p-hydroxyphenyl)ethane, hexafluorobisphenol A, tetramethylbisphenol (4,4'-dihydroxy-3,3',5,5'-tetramethyl bisphenol), 1,5-dihydroxynaphthalene, 1,1',7,7'-tetrahydroxy-dinaphthyl methane, 4,4'-dihydroxy-α-methylstilbene, a condensation product of Bisphenol A with formaldehyde (Bisphenol A novolac), a condensation product of phenol with formaldehyde, preferably Bisphenol F (mixture of o,o', o,p' and p,p' isomers of dihydroxy diphenylmethane), a condensation product of cresol with formaldehyde (mixtures of o,o', o,p' and p,p' isomers of methyl hydroxy diphenylmethane), an alkylation product of phenol and dicyclopentadiene (2,5-bis[(hydroxy phenyl]octahydro-4,7-methano-5H-indene), a condensation product of phenol and glyoxal (tetrakis(4-hydroxy-phenyl) ethane), a condensation product of phenol and a hydroxybenzaldehyde (e.g., tris(4-hydroxyphenyl)methane), 1,1,3-tris-(p-hydroxyphenyl)-propane, and mixtures thereof.

The polyamines can be aliphatic or aromatic. Aromatic diamines are preferred, like for instance 4,4'-diamino diphenyl methane.

The amino alcohol can be aliphatic or aromatic. Aromatic amino alcohol are preferred like for instance, p-aminophenol.

The imides and amides can be aliphatic or aromatic. Heterocyclic imides and amides are preferred, like for instance 1,3,5-triazinetriol and imidazolidine-2,4-dione.

Polycarboxylic acids can be aliphatic or aromatic. An example of dimeric fatty acid is linoleic dimer acid. The polycarboxylic acid is preferably an aromatic dicarboxylic acid like for instance hexahydrophthalic acid.

1.3. Processes for Making Epoxy Derivatives

The process for making epoxy resins, glycidyl ethers and glycidyl esters generally involve a reaction of the product containing epichlorohydrin and the compound containing at least one active hydrogen atom, followed by dehydrochlorination with a basic agent The process for making epoxy resin usually involves two steps: the preparation of an uncured epoxy resin followed by a curing step.

1.3.1. Uncured ER

The reaction between the product containing epichlorohydrin and the compound containing at least one, preferably two active hydrogen atoms can be carried out by any process known in the art like for instance the Caustic Coupling Process and the phase-transfer catalyst process, for making Liquid Epoxy Resins (LER), the Taffy and the Advancement or Fusion process for making Solid Epoxy Resins (SER).

Caustic Coupling Process

In the caustic process, caustic is used as a catalyst for the nucleophilic ring-opening (coupling reaction) of the epoxide group on the primary carbon atom of epichlorohydrin by the phenolic hydroxyl group and as a dehydrochlorinating agent for conversion of the chlorohydrin to the epoxide group. Caustic (NaOH) can however be substituted by any basic compound.

The epichlorohydrin and the compound with active hydrogen atom, preferably an aromatic hydroxyl or aromatic amine compound, are employed in a molar ratio of from about 2:1 to about 10:1, preferably from about 2:1 to about 6:1, respectively.

The basic compound may be an organic or inorganic basic compound. Organic basic compounds are for example amines, phosphines and ammonium, phosphonium or arsonium hydroxides. Inorganic basic compounds are preferred. The expression "inorganic compounds" is understood to mean compounds which do not contain a carbon-hydrogen bond. The inorganic basic compound may be chosen from alkali and alkaline-earth metal oxides, hydroxides, carbonates, hydrogencarbonates, phosphates, hydrogenphosphates and borates, and mixtures thereof. Alkali and alkaline-earth metal oxides and hydroxides are preferred. Preferred alkali metal hydroxides which can be employed herein include, for example, sodium hydroxide, potassium hydroxide, lithium hydroxide or mixtures thereof. Sodium hydroxide is especially preferred.

In the process according to the invention, the basic compound may be in the form of a liquid, an essentially anhydrous solid, a hydrated solid, an aqueous and/or organic solution or an aqueous and/or organic suspension. The basic compound is preferably in the form of an essentially anhydrous solid, a hydrated solid, an aqueous solution or an aqueous suspension. It is preferred to use a solution or a suspension, preferably a solution of the basic compound, preferably sodium hydroxide, in water.

The content of the basic agent in the solution or suspension is generally higher than or equal to 5% by weight, preferably higher than or equal to 10% by weight, preferably higher than or equal to 20% by weight, and most preferably higher than or equal to 30% by weight. That content is usually lower than or equal to 70% by weight, preferably lower than or equal to 60% by weight, preferably lower than or equal to 50% by weight, and most preferably lower than or equal to 40% by weight.

The alkali metal hydroxide is preferably employed as an aqueous solution, usually at a concentration of from about 20 to about 50, preferably from about 40 to about 50 percent by weight.

The amount of basic compound, preferably alkali metal hydroxide, which is employed in the process of the present invention is from about 0.80 mole to about 1.2 mole of basic agent, preferably from about 0.90 mole to 1.0 mole per each, preferably aromatic, hydroxyl group and, preferably aromatic, amine hydrogen.

The basic agent, epichlorohydrin and the compound containing active hydrogen atom can be mixed in any order. It is preferred to add the basic compound to a mixture of the two other reactants. The basic agent, preferably, alkali metal hydroxide can be added either continuously or incrementally, but never is all of the alkali metal hydroxide added in one increment.

The reaction can be carried out in a solvent. Suitable solvents which can be employed include any solvent which does not react with any component in the reaction mixture. Preferably such solvent is partially or wholly miscible with water, forms a codistillate with the epichlorohydrin and water and the distillate has a boiling point below that of the lowest boiling component of the reaction mixture at the pressure employed. Suitable such solvents include primary and secondary alcohols such as, for example, 1-methoxy-2-hydroxy propane, 1-butoxy-2-hydroxy ethane, cyclohexanol. The secondary alcohols are preferred.

When a solvent is used, the amount of solvent which is employed will depend on the particular solvent and the compound containing active hydrogen atom being employed. The solvent generally ranges from about 5 to about 50 weight percent, preferably from about 10 to about 40 weight percent based on the total weight of reactants.

The pressure can be equal to 1 bar absolute, lower than 1 bar absolute or higher than 1 bar absolute. When a solvent is used, suitable pressures which can be employed are those which will provide the codistillate with a boiling point of from about 45° C. to about 80° C., preferably from about 55° C. to about 70° C.

The temperature of the reaction is usually greater than or equal to 25° C., preferably greater than or equal to 50° C., more preferably greater than or equal to 90° C., and most preferably greater than or equal to 95° C. The temperature of the reaction is usually lower than or equal to 200° C., preferably lower than or equal to 150° C., more preferably lower than or equal to 125° C., and most preferably lower than or equal to 120° C.

The reaction is usually conducted for a length of time such that the quantity of groups containing active hydrogen atom remaining in the reaction mixture is not greater than about 0.5, preferably not greater than about 0.2 percent by weight. That time is usually greater than or equal to 0.5 h, frequently greater than or equal to 1.0 h, often greater than or equal to 2.0 h, and most particularly greater than or equal to 3.0 h. The time of reaction is usually lower than or equal to 20 h, often lower than or equal to 10 h, frequently lower than or equal to 5 h, and most particularly lower than or equal to 4 h.

Upon completion of the reaction, the resultant epoxy resin is finished in any of the methods normally employed. The excess epichlorohydrin is usually removed by distillation and the salt removed by filtration, centrifugation and/or water washing.

The epichlorohydrin distillation is generally carried out in two steps. The first step is carried out generally at atmospheric pressure (1 bar absolute), at a temperature usually greater than or equal to 100° C., preferably greater than or equal to 120° C., more preferably greater than or equal to 130° C., and most preferably greater than or equal to 145° C. and usually lower than or equal to 200° C., preferably lower than or equal to 180° C., more preferably lower than or equal to 175° C., and most preferably lower than or equal to 155° C. The second step is carried out usually at a subatmospheric pressure, usually lower than or equal to 0.1 bar absolute, preferably lower than or equal to 0.01 bar, more preferably lower than or equal to 0.005 bar, and most preferably lower than or equal to 0.002 bar, at a temperature usually greater than or equal to 150° C., preferably greater than or equal to 170° C., more preferably greater than or equal to 190° C., and most preferably greater than or equal to 195° C. and usually lower than or equal to 300° C., preferably lower than or equal to 250° C., more preferably lower than or equal to 220° C., and most preferably lower than or equal to 215° C.

The salt which is formed can be separated from the crude product through addition of a solvent, e.g. toluene, followed by filtration and distillation to remove the solvent.

Phase-Transfer Catalytic Process

Alternatively, in the Phase-Transfer Catalyst Process, the coupling reaction and dehydrochlorination can be performed separately by using phase-transfer coupling catalysts, such as quaternary ammonium salts, which are not strong enough bases to promote dehydrochlorination. Once the coupling reaction is completed, caustic is added to carry out the dehydrochlorination step. Via this method, higher yields of for example the monomeric diglycidyl ether of Bisphenol A (DGEBA) (>90%) are readily available.

Batch methods and preferably continuous or semi continuous processes can be used.

Taffy Process

The Taffy method is used to prepare higher molecular weight solid resins. It is directly from epichlorohydrin, the compound containing active hydrogen atoms, and a stoichiometric amount of NaOH. This process is very similar to the caustic coupling process used to prepare liquid epoxy resins. Lower epichlorohydrin to compound containing active hydrogen atoms ratios are used to promote formation of high molecular weight resins. Upon completion of the polymerization, the mixture consists of an alkaline brine solution and a water resin emulsion. The product is recovered by separating the phases, washing the resin with water, and removing the water under vacuum.

The epichlorohydrin and the compound with active hydrogen atom, preferably an aromatic hydroxyl or aromatic amine compound, are employed in a molar ratio of from about 1:1 to about 2:1, preferably from about 1.3:1 to about 1.8:1, respectively.

The alkali metal hydroxide is preferably employed as an aqueous solution, usually at a concentration of from about 1 to about 20, preferably from about 5 to about 15 percent by weight.

The amount of basic compound, preferably alkali metal hydroxide, which is employed in the process of the present invention is from about 0.05 mole to about 2 mole of basic agent, preferably from about 0.1 mole to 0.5 mole per each, preferably aromatic, hydroxyl group and, preferably aromatic, amine hydrogen.

The temperature of the reaction is usually greater than or equal to 25° C., preferably greater than or equal to 50° C., more preferably greater than or equal to 90° C., and most preferably greater than or equal to 95° C. The temperature of the reaction is usually lower than or equal to 200° C., preferably lower than or equal to 150° C., more preferably lower than or equal to 125° C., and most preferably lower than or equal to 120° C.

The time of reaction is usually greater than or equal to 0.1 h, frequently greater than or equal to 0.5 h, often greater than or equal to 1.0 h, and most particularly greater than or equal to 1.5 h. The time of reaction is usually lower than or equal to 20 h, often lower than or equal to 10 h, frequently lower than or equal to 5 h, and most particularly lower than or equal to 4 h.

The basic agent, epichlorohydrin and the compound containing active hydrogen atom can be mixed in any order. It is preferred to add epichlorohydrin to a mixture of the two other reactants.

The reaction is usually carried out under vigorous agitation.

At the end of the reaction, the mixture separates into two layers. The heavier aqueous layer is drawn off and the molten, taffy-like product is washed with hot water until the wash water is neutral. The taffy-like product is dried at a temperature generally higher than or equal to 100° C., preferably higher than or equal to 120° C.

Alternatively, epichlorohydrin and water can be removed by distillation at temperatures up to 180° C. under vacuum. The crude resin/salt mixture can then be dissolved in a secondary solvent to facilitate water washing and salt removal. The secondary solvent can then be removed via vacuum distillation to obtain the product.

The advancement or fusion process is an alternative method for making solid epoxy resin and is based on the chain-extension reaction of liquid epoxy resin (for example, crude DGEBA) with bisphenol A.

1.3.2. Curing Agents

The curing of Epoxy Resins can be carried out using classical curing agents. The cure can be done with coreactive curing agents, or it can be catalytic or photoinitiated cationic.

The coreactive curing agents can be selected from amine functional curing agents, carboxylic functional polyester and anhydride curing agents, phenolic-terminated curing agents, melamine-, urea-, and phenol-formaldehyde resins, mercaptans (polysulfides and polymercaptans) curing agents, cyclic amidines curing agents, isocyanate curing agents and cyanate ester curing agents The amine functional curing agents can be primary and secondary amines, polyamides, amidoamines and dicyandiamide.

The amines can be aliphatic, cycloaliphatic, aromatic amines or arylyl amines.

The aliphatic amines can be selected from liquid aliphatic polyamines, such as polyethylene polyamines, hexamethylene diamine, polyether amines (polyglycol-based polyamines), ketimines (reaction products of ketones and primary aliphatic amines), mannich base adducts (reaction products of amine, phenol and formaldehyde), polyetheramines (reaction product of polyols derived from ethylene or propylene oxide with amines) and mixtures thereof.

The cycloaliphatic amines can be selected from isophorone diamine, bis(4-amino-cyclohexyl)methane, 1,2-diamino-cyclohexane, trihexylmethylene diamines, metaxylylenediamine, and mixtures thereof.

The aromatic amines can be selected from meta-phenylenediamine, methylene dianiline, alkyl(tetraethyl-)-substituted methylene dianiline, 4,4'-diaminodiphenylmethane, 4,4'-diamino diphenyl sulfone, diethylenetoluenediamine The arylyl amines can be selected from meta xylylenediamine, 1,3-bis(aminomethyl cyclohexane).

The amine can be more specifically selected from diethylenetriamine, triethylenetetramine, Poly(oxypropylene diamine), poly(oxypropylene triamine), poly(glycol amine), N-aminoethylpiperazine, isophorone diamine, 1,2-diaminocyclohexane, bis(4-aminocyclohexyl)methane, 4,4-diamino-diphenylmethane, 4,4-diaminodiphenyl sulfone, m-phenylenediamine, diethyltoluenediamine, meta-xylene diamine, 1,3-bis(aminomethyl cyclohexane, and mixtures thereof.

The polyamides can be obtained by reaction of dimerized and trimerized vegetable oil fatty acids (9,12 and 9,11-linoleic acids) with polyamines (diethylene triamine) or from polyamines and phenolic-containing carboxylic acids (phenalkamines).

The amidoamines can be obtained by reaction of mono functional acid like tall-oil fatty acid with a polyamine such diethylenediamine.

The carboxylic functional polyester can be obtained by reaction of terphthalic acid, trimellitic anhydride and neopentyl alcohol The acid anhydrides can be phthalic anhydride, tetrahydrophthalic anhydride, methyltetrahydrophthalic anhydride, methyl hexahydrophthalic anhydride, hexahydrophthalic anhydride, nadic methyl anhydride or methyl himic anhydride, benzophenonetetracarboxylic dianhydride, tetrachlorophthalic anhydride, and mixtures thereof.

The phenolic-terminated curing agents are products that can be obtained by reaction of phenol, creseol or bisphenol a with formaldehydes.

The mercaptans (polysulfides and polymercaptans) curing agents generally contain terminal thiols.

The cyclic amidines curing agents can be for instance 2-phenyl imidazolidine.

The cyanate ester curing agents can be for instance bisphenol a dicyante ester.

The catalytic cure can be carried out with Lewis bases or Lewis acids.

The Lewis bases are for instance tertiary amine, like 2-diethylamino-methylphenol, 2,4,6-tris(dimethylaminomethyl) phenol and imidazoles such as 2-methylimidazole and 2-phenylimidazole, cyclic amidines like 2-phenylimidazo line, substituted ureas like 3-phenyl-1,1-dimethylurea and quaternary ammonium salt like tetralkyl- and alkyl-triphenyl phosphonium salts.

The Lewis acid can be selected from boron trilhalides, preferably boron trifluoride.

The Photoinitiated Cationic Cure can be carried out with photoinitiators like aryldiazonium salts, diaryldiazonium salts, diaryldiionium salts and onium salts of Group VIa elements, such as triarylsulfonium salt, dialkylphenacyl sulfonium salts.

1.4 Uses of Epoxy Resins

The epoxy resins can be used in coating applications and in structural applications. The coating applications can be in the fields of marine and industrial maintenance (corrosion-resistant coatings for ships, shipping containers, offshore oil rigs and platforms, transportation infrastructures such as bridges, rail car coatings, coatings for industrial storage tanks, and primers for light industrial and agricultural equipment), metal container (aluminum and steel food and beverage cans) and coil coatings (metal can ends, can bodies, building products, appliance panels, transportation, and metal furniture applications), automotive coatings (primer surface coatings) and inks and resists. Coating can be done using various technologies like low solids solventborne coating, high solid solventborne coating, solvent-free coating, waterborne coating, powder coating and radiation-curable coating.

The structural applications can be in the field of structural composites (fiber reinforcing materials based on glass, boron, graphite and aromatic polyaramides), of civil engineering, flooring (floor paints, self-leveling floors, trowelable floors, and pebble-finished floors) and construction, of electrical laminates, of electrical laminates (printed wiring boards and printed circuit boards), of other electrical and electronic applications, like casting, potting, encapsulation (switchgear components, transformers, insulators, high voltage cable accessories, and similar devices) and transfer molding (encapsulation of electronic components such as semiconductor chips, passive devices, and integrated circuits), of adhesives (cohesion between similar and dissimilar materials such as metals, glass, ceramics, wood, cloth, and many types of plastics) and of tooling (prototypes, master models, molds and other parts for aerospace, automotive, foundry, boat building, and various industrial molded items).

1.5 Uses of Glycidyl Ethers and Esters

These products are used for applications such as coatings, adhesives and reactive diluents.

1.6 Uses of Glycidyl Amides and Imides

These products are used for applications such as outdoor powder coatings with polyesters, or in applications in which a non-yellowing epoxy resin is desirable.

2. PRODUCTS FOR FOOD-DRINK APPLICATIONS

Coagulants

2.1. General

The product containing epichlorohydrin according to the invention can be used for the manufacture of products that will be used in applications where they will come in contact with food and drink, more specifically for the manufacture of synthetic organic coagulants.

Coagulation refers to the reduction or elimination of electrostatic repulsion forces between particles via addition of certain coagulants, and in technical terms, the first phase of floc formation after chemical mixing and destabilization, but before dosing of flocculants.

Coagulants are generally polymers with a high cationic charge density to neutralize negative charges of colloids and initiate the formation of flocs. They generally exhibit a relatively low molecular weight in order to permit a good diffusion of the charges around the particles and a low viscosity to allow a good distribution of the polymer in the effluents.

By coagulant, one intends to denote a polymer, comprising at least one repeat unit containing at least one 2-hydroxypropyldialkylammonium group.

Figure 5:
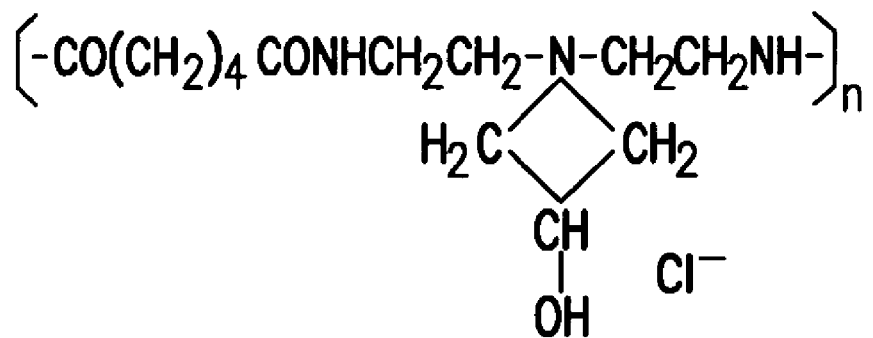
FIG. 5: example of chemical formula of a coagulant molecule

An example of a coagulant molecule is presented in FIG. 5.

2.2. Co-Reactants

In the application according to the invention, the product containing epichlorohydrin is usually subjected to a reaction with ammonia, an amine, a polyaminoamide or a polyimine.

The amine can be a mono-, a di- or a polyamine. The amine can be aliphatic, alicyclic or aromatic, saturated or unsaturated, linear or substituted. The amine has preferably at least one, more preferably at least two primary amino hydrogens.

The amine can be represented by the general formula:

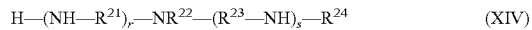

$$H-(NH-R^{21})_r-NR^{22}-(R^{23}-NH)_s-R^{24} \quad (XIV)$$

wherein $R^{22}$ and $R^{24}$ can be equal, except when equal to H, or different and can independently be selected from H, alkyl or alkenyl radical, linear, branched or carbocyclic, having from 1 to 30 carbon atoms, $R^{21}$ and $R^{23}$ can be equal or different, preferably equal, divalent aliphatic radical aromatic radicals having from 2 to 12 carbon atoms, each of r and s is an integer of from 0 to 6, r plus s equals 0 to 6.

Amines include lower alkyl and lower alkenyl primary monoamines, such as methylamine, ethylamine, isopropylamine, tertbutylamine, mixed amylamines, n-octylamine, branched-chain nonylamine, secondary amines such as dimethylamine, ethylmethylamine, diethylamine, propylmethylamine, propylethylamine, dipropylamine, dibutylamine, propylbutylamine, ethylbutylamine, methylbutylamine, pentylethylamine, pentylethylamine, and pentylpropylamine, tertiary amines, as well as alkylenediamines, triamines and polyamines, with or without an alkenyl or alkyl substituent bonded to nitrogen, such as ethylenediamine, propylenediamine, butylenediamine, pentylenediamine, hexylenediamine, octylenediamine, dodecylenediamine, cyclohexylenediamine, diethylenetriamine, dipropylenetriamine, dipentylenetriamine, triethylene tetramine, tributylenetetramine, trihexylenetetramine, tetraethylenepentamine, tetrapropylenepentamine, pentahexylenehexamine, pentapropylenehexamine, N-ethyl-1,2-ethylenediamine, N-(2-propenyl)-1,3-propanediamine, N-hexyl-1,4-butanediamine, N-2-ethylhexyl-1,3-propanediamine, N-(5-octenyl)-1,6-hexanediamine, N-butyltriethylenetriamine, N-hexyltripropylenetetramine, N-nonyltetrabutylenepentamine and N-(oleyl)-heaxethyleneheptamine, N-alkyl-1,3-diaminopropane, butane and hexane, where the radical alkyl can be hexyl, heptyl, octyl, nonyl, decyl, undecyl, dodecyl, tridecyl, tetradecyl, pentadecyl, hexadecyl, heptadecyl, nonadecyl, eicosyl, heneicosyl, docosyl, tricosyl, and tetracosyl.

The monoamine is preferably a secondary amine, more preferably dimethylamine.

The diamine is more preferably selected from 1,2-diaminoethane, 1,2-diaminopropane, 1,3-diaminopropane, a N-substituted diaminopropane, more preferably, 1-amino-3-dimethylaminopropane, 1-amino-3-diethylaminopropane, 1-amino-3-cyclohexylaminopropane, N,N,N',N'-tetramethyl-1,3-propanediamine, 1,3-diaminobutane, 1,5-diaminopentane, 1,8-diaminooctane, 1,10-diaminodecane, 1,12-diaminododecane, 2-(diethylamino)ethylamine, 1-diethylamino-4-aminopentane, 3-aminomethyl-3,5,5-trimethylcyclohexylamine and N,N,N',N',-tetramethyl-1,6-hexanediamine.

Polyaminoamides are generally obtained from polyamide, preferably polyacrylamide, formaldehyde and an amine, preferably a secondary amine. Poly[N-(dialkylaminoalkyl) acrylamide] is particularly preferred.

Polyimines are usually obtained by ring opening polymerization of alkylene imine, preferably ethylene imine.

2.3. Processes

The reaction between the product containing epichlorohydrin and the compound containing at least one, preferably two primary amino hydrogens can be carried out by any process known in the art.

The reaction is generally carried out in the liquid phase, possibly in the presence of a solvent. The solvent may be selected from water, an organic solvent, preferably miscible with water, or mixtures thereof. Water is preferred. Monoalcohols, like methanol, ethanol, n-propanol, isopropanol and butanol are preferred organic solvents When a solvent is used, the ammonia or amine content in the solvent-ammonia or amine mixture is usually higher than or equal to 5% by weight (% wt), preferably higher than or equal to 10 wt %, more preferably higher than or equal to 20 wt % and most preferably higher than or equal to 45 wt %. That content is usually lower than or equal to 90 wt %, preferably lower than or equal to 75 wt %, more preferably lower than or equal to 60 wt %, and most preferably lower than or equal to 55 wt %.

The molar ratio between epichlorohydrin and ammonia or amine is generally higher than or equal to 0.1, preferably higher than or equal to 0.5, more preferably higher than or equal to 0.75 and most preferably higher than or equal to 1. That ratio is usually lower than or equal to 10, preferably lower than or equal to 5, more preferably lower than or equal to 3, and most preferably lower than or equal to 2.

The temperature at which the reaction is carried out is generally higher than or equal to 10° C., preferably higher than or equal to 25° C., more preferably higher than or equal to 50° C. and most preferably higher than or equal to 60° C. That temperature is usually lower than or equal to 120° C., preferably lower than or equal to 110° C., more preferably lower than or equal to 100° C., and most preferably lower than or equal to 90° C.

The pressure at which the reaction is carried out is generally higher than or equal to 0.1 bar absolute, preferably higher than or equal to 0.2 bar, more preferably higher than or equal to 0.5 bar and most preferably higher than or equal to 1 bar. That pressure is usually lower than or equal to 20 bar, preferably lower than or equal to 10 bar, more preferably lower than or equal to 5 bar, and most preferably lower than or equal to 2 bar.

The duration of the reaction is generally higher than or equal to 10 min absolute, preferably higher than or equal to 20 min, more preferably higher than or equal to 30 min and most preferably higher than or equal to 60 min. That duration is usually lower than or equal to 10 h, preferably lower than or equal to 5 h, more preferably lower than or equal to 3 h, and most preferably lower than or equal to 2 h.

The manufacturing procedure usually involves the dissolution of the amines or ammonia in the solvent, followed by a slow addition of the epichlorohydrin, itself possibly dissolved in a solvent, possibly cooling in order to keep the temperature of the reaction between 10 and 50° C., often between 25 and 40° C., then after the epichlorohydrin addition is complete, raising the temperature to between 60 and 90° C.

The reaction product can be recovered as an aqueous solution, or a solid after further treatments, e.g. distillation of the solvents under vacuum, treatment of the solution with an acid or a base.

These reactions lead to the formation of the monomer. For example a reaction between epichlorohydrin and dimethylamine produces the epichlorohydrin dimethylamine monomer. This is then homopolymerized to the corresponding quaternary ammonium compound which is a low molecular weight cationic polymer used as a coagulant. Such polymerization usually takes place under alkaline conditions.

The monomer can also be copolymerized with acrylamide to produce higher molecular weight polymers also used for water treatment.

2.4. Products Characteristics

The obtained polymers usually exhibit a molecular weight that is higher than or equal to 5 000, often higher than or equal to 10 000, and frequently higher than or equal to 50 000. That molecular weight is usually lower than or equal to 500 000, often lower than or equal to 400 000, and frequently lower than or equal to 300 000. They can be obtained as aqueous solution containing from 40 to 50% by weight of polymers and exhibiting viscosities from 40 to 11 000 centipoise.

2.5. Uses

These polymers can be used for treatment of raw water for conversion to drinking water, for recycling paper of water in Pulp & Paper Industry, for paint detackification, for breaking oil emulsions, for oil and grease removal, and for sludge dewatering. They can also be used for sugar refining.

3. PRODUCTS FOR FOOD-DRINK APPLICATIONS

Wet-Strength Resins

3.1. General

The product containing epichlorohydrin according to the invention can be used for the manufacture of products that will be used in applications where they will come in contact with food and drink, more specifically for the manufacture of wet-strength resins.

By wet-strength resin one intends to denote a polyaminoamide polymer, the chemical formula of which contains at least one group selected from 2,3-epoxypropylamine, 2,3-epoxypropylammonium, 3-chloro-2-hydroxypropylamine, 3-chloro-2-hydroxypropylammonium, 3-hydroxyazetidinium, and any combination of at least two of them.

Figure 6:
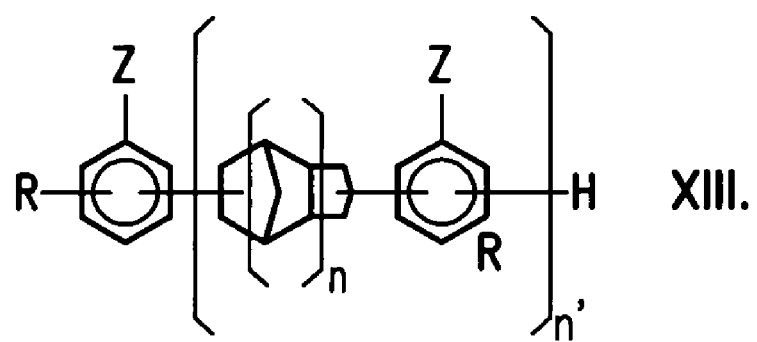
FIG. 6: example of chemical formula of wet-strength resin polymers
Figure 6:
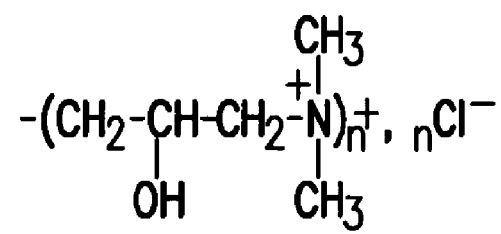

Examples of chemical formulas of such a polymer are presented in FIG. 6.

3.2. Co-Reactants

In the application according to the invention, the product containing epichlorohydrin is usually subjected to a reaction with a polyamine or a polyamide.

The polyamine and the reactions conditions are as described above for the manufacture of coagulants.

The polyamide is usually obtained by reacting an amine, preferably a polyalkylene polyamine (in this case the polyamide is generally referred as a polyaminamide) and a dicarboxylic acid, preferably a saturated aliphatic dicarboxylic acid, as described in U.S. Pat. No. 865,727, the content of which is incorporated herein by reference. The polyamide may be represented by the general formula

—NH—($R^{21}$)$_r$—$NR^{22}$—($R^{23}$—NH)$_s$—$COR^{24}$CO—  (XV)

where $R^{21}$, $R^{22}$, $R^{23}$, r and s are as described above, and $R^{24}$ is the divalent hydrocarbon radical of the dibasic carboxylic acid, preferably selected from phenylene, naphthalene, methylene, ethylene, propylene, butylenes, pentylene, hexylene, octylene and nonylene.

Preferably, the polyamide may be represented by the general formula

—NH($C_tH_{2t}$HN)$_x$—$COR^{24}$CO—  (XVI)

wherein t and x are each 2 or more and wherein the —NH($C_tH_{2t}$HN)$_x$— group is derived from the polyamines described above, preferably containing from 2 to 8 alkylene groups, more preferably from diethylenetriamine, triethylenetetramine, tetraethylenepentamine, dipropylenetriamine and N-bis(aminopropyl)methylamine the —$COR^{24}$CO— group is derived from dibasic carboxylic acid containing from 2 to 12 carbon atoms, preferably selected from phenylene, naphthalene, methylene, ethylene, propylene, butylenes, pentylene, hexylene, octylene and nonylene. The acid is more preferably selected from malonic, succinic, glutaric, adipic, diglycolic, sebacic or azelaic acid, and mixtures thereof

3.3. Processes

The reaction between the polyamide and epichlorohydrin is usually carried out at a temperature generally higher than or equal to 45° C. That temperature is usually lower than or equal to 100° C., preferably lower than or equal to 70° C. The temperature at which the reaction is conducted is preferably selected in two stages. In the first stage, the reaction mixture is maintained at 30° C.-50° C., preferably 39°-41° C. Reaction time for the first stage is preferably about 90-190 minutes to form an intermediate polyaminochlorohydrin. Then the reaction temperature is gradually increased to 55°-75° C. such that the intermediate polyaminochlorohydrin is controllably cross-linked to a determined level. The second stage is continued until the viscosity of the reaction mixture reaches the desired level (preferably level M to N on a Gardner-Holdt viscosity scale).

Broadly speaking, the reaction can be carried out neat or in an aqueous solution of up to 57 wt % in water. Preferably, the polyaminoamide is reacted with epichlorohydrin in an aqueous solution of 52-57 wt % in water that is, a solution of 43-48 wt % total solids (the weight percentage of the solution that is solubilized solid material), more preferably about 45 wt % total solids. Reaction time varies depending on the temperature, with lower temperatures taking longer times. The typical composition of these resins is 12.5% (10-40% solids). However, due to the cost of transporting water, companies have tried to produce resin solutions of higher concentration. It appears that at least one of the main issues making such concentrated solutions difficult to prepare is their high content of dichloropropanol so the level of this impurity is exceeded in the final application.

Reaction is preferably carried out until all, or substantially all of the available amine groups on the polyaminoamide are reacted with epichlorohydrin. Generally, reaction times vary between about 1 and 19 hours, preferably between 3 and 6 hours. Because the reaction is exothermic, the epichlorohydrin is added slowly over time to the polyaminoamide to allow for more effective heat transfer from the reaction medium. Heat transfer from the reaction medium can be accomplished according to known procedures, such as immersing the reaction vessel in a refrigerated environment, e.g., an ice bath, or passing refrigerated coils inside the reaction vessel.

The reaction is usually carried out in aqueous solution to moderate the reaction. The pH adjustment is usually not necessary but since the pH decreases during the reaction, it may be desirable in some cases, to add alkali to combine with at least some of the acid formed.

In the reaction, it is preferred to use sufficient epichlorohydrin to convert the entire secondary amine group to tertiary amine groups. The molar ratio between epichlorhydrin and the secondary amine groups is usually higher than or equal to 0.1, preferably higher than or equal to 0.5, and more preferably higher than or equal to 1. That molar ratio is usually lower than or equal to 10, preferably lower than or equal to 5, and more preferably lower than or equal to 2.

The reaction between the polyamide and epichlorohydrin can also be carried in the presence of a quaternizing agent, the conditions of reaction and the reactants, except for the inclusion of the quaternizing agent, being essentially the same as described above. In a preferred procedure, the epichlorohydrin is first added to an aqueous solution of the polyamide at a temperature from 45 to 55° C. The reaction mixture is then heated to a temperature from about 60 to 100° C., and preferably from about 50 to 80° C., depending on the rate of the polymerization desired. After a suitable time at that temperature, i.e., 0 to 100 min, a time after which the epoxy group of the epichlorohydrin have reacted with the secondary amine groups of the polyamide, the quaternizing agent is added and the reaction mixture heated, preferably at a temperature from 60° C. to 80° C. The pH of the reaction mixture is then reduced to 4, preferably between 2 and 3 with any suitable acid such as sulphuric, hydrochloric formic and the like. The amount of quaternizing agent should be sufficient to convert from 25% to 75%, preferably 50% of the tertiary amine group to quaternary group.

The quaternizing agent may be any compound capable of quaternizing a tertiary nitrogen atom in an aqueous medium. In general these compounds are characterized by having as a principal part of their structure an alkyl group or substituted alkyl group which is readily available for alkylation under the conditions herein described. These include the lower alkyl esters of mineral acids such the halides, sulfates and phosphates, and substituted alkyl halides. Illustrative of these compounds which may be used are dimethyl, diethyl and dipropylsulfate, methyl chloride, methyl iodide, methyl bromide, ethyl bromide, propyl bromide, the mono-, di- or trimethyl, ethyl and propyl phosphates, 1,3-dcihloropropanol-2 and 1-chloroglycerol. Certain aromatic compounds may also be used like benzyl chloride and methyl p-toluene sulfonate.

The above products resulting from the reaction between epichlorohydrin and the polyamide can be further cross polymerized by treatment with a sodium carbonate or sodium hydroxide solution at a pH between 10.5 and 12.

3.4. Uses

These resins are used in papers that will get wet such as paper towels, tea bags, coffee filters, milk cartons, meat wrapping, wallpaper. They can also be used in the production of high fructose corn syrup and to prevent wool from shrinking

4. CATIONIZATION AGENTS

4.1. General

The product containing epichlorohydrin according to the invention can be used for the manufacture of cationization agents.

By cationization agent, one intends to denote a quaternary ammonium salt, the chemical formula of which contains at least one group selected from 2,3-epoxypropyl, 3-chloro-2-hydroxypropyl, and their combination, and which is not a polymer.

Cationization agents are often quaternary ammonium salt containing a glycidyl or a 3-chloro-2-hydroxypropyl group attached to the nitrogen atom. The cationization agent can be isolated as solids or as solution in water or in organic solvents.

Examples of cationization agents are 3-chloro-2-hydroxypropyl trimethylammonium chloride and glycidyl trimethyl ammonium chloride.

4.2. Co-Reactants

In the application according to the invention, the product containing epichlorohydrin is usually subjected to a reaction with an amine, an amine salt, or a mixture thereof.

The amine is preferably a tertiary amine and the amine salt is preferably a tertiary amine salt.

The tertiary amine salt is for instance a salt obtained by treating an amine with an acid, preferably an inorganic acid, like for instance hydrochloric or sulphuric acid.

The tertiary amine may be represented by the formula

$$R^{31}—N(R^{32})—R^{33} \quad (XVII)$$

wherein $R^{31}$, $R^{32}$ and $R^{33}$ can be selected from the group consisting of alkyl, cycloalkyl, alkene, aryl, aralkyl, alkylaryl, two of them being possibly joined to form a ring and containing from 1 to 25 carbon atoms. The group attached to the nitrogen can be linear or substituted, saturated or unsaturated.

If all three of $R^{31}$, $R^{32}$ and $R^{33}$ are the same, they preferably each should not contain more than 4 carbon atoms. If all three of $R^{31}$, $R^{32}$ and $R^{33}$ are not the same and if $R^{33}$ contains up to 18 carbon atoms, the $R^{31}$ and $R^{32}$ should preferably be of the group consisting of methyl and ethyl. If $R^{31}$ and $R^{32}$ are joined to form a ring, then $R^{33}$ should preferably be from the group consisting of methyl and ethyl.

Examples of suitable tertiary amines are triethylamine, N-methyl and N-ethylmorpho line, N-ethyl and N-methylpiperidine and methyl diallylamine, trimethylamine, dimethylbenzylamine, dimethyldodecylamine, dimethylstearylamines, dimethylaniline, tri-npropylamine.

It is particularly preferred that the tertiary amine possess two methyl groups attached to the nitrogen, like for instance, trimethylamine, dimethylbenzylamine, dimethyldodecylamine, dimethylstearylamine, and dimethylaniline.

The amine salt is preferably a salt obtained by reaction between the above described amines with hydrochloric or sulfuric acid, preferably with hydrochloric acid.

4.3. Processes

The reaction between the product containing epichlorohydrin and the amine or the amine salt can be carried out by any process known in the art such as those described in U.S. Pat. No. 2,876,217 the content of which is incorporated herein by reference.

The reaction is generally carried out in the liquid phase, possibly in the presence of a solvent. The solvent may be selected from water, an organic solvent e.g. an alcohol, a ketone, an ester or an aliphatic hydrocarbon, preferably miscible with water, or mixtures thereof. Water is preferred. Monoalcohols, like methanol, ethanol, n-propanol, isopropanol and butanol are preferred organic solvents, with methanol being particularly preferred.

The content of epichlorohydrin in the solvent is usually higher than or equal to 0.1 mol/l, often higher than or equal to 0.5 mol/l, frequently higher than or equal to 1.0 mol/l, particularly higher than or equal to 2 mol/l, specifically higher than or equal to 5 mol/l and sometimes higher than or equal to 10 mol/l. That epichlorohydrin content is usually lower than 20 mol/1.

The content of amine or amine salt in the solvent is usually higher than or equal to 0.1 mol/l, often higher than or equal to 0.5 mol/l, frequently higher than or equal to 1.0 mol/l, particularly higher than or equal to 2 mol/l, specifically higher than or equal to 5 mol/l and sometimes higher than or equal to 10 mol/1. That amine or amine salt content is usually lower than 20 mol/l.

The molar epichlorohydrine/amine or amine salt ratio is usually higher than or equal to 0.1, preferably higher than or equal to 0.5, more preferably higher than or equal to 1 and most preferably higher than or equal to 1.2. That ratio is usually lower than or equal to 10, more preferably lower than or equal to 5 and lost preferably lower than or equal to 2.

The temperature at which the reaction is carried out is generally higher than or equal to 0° C., preferably higher than or equal to 10° C., more preferably higher than or equal to 25° C. and most preferably higher than or equal to 40° C. That temperature is usually lower than or equal to 100° C., preferably lower than or equal to 80° C., more preferably lower than or equal to 60° C., and most preferably lower than or equal to 50° C.

The pressure at which the reaction is carried out is generally higher than or equal to 0.1 bar absolute, preferably higher than or equal to 0.2 bar, more preferably higher than or equal to 0.5 bar and most preferably higher than or equal to 1 bar. That pressure is usually lower than or equal to 20 bar, preferably lower than or equal to 10 bar, more preferably lower than or equal to 5 bar, and most preferably lower than or equal to 2 bar.

The duration of the reaction is generally higher than or equal to 10 min absolute, preferably higher than or equal to 20 min, more preferably higher than or equal to 30 min and most preferably higher than or equal to 60 min. That duration is usually lower than or equal to 72 h, preferably lower than or equal to 60 h, more preferably lower than or equal to 48 h, and most preferably lower than or equal to 10 h.

When an amine salt or a mixture of an amine and of an amine salt is used, the pH of the reaction is usually at least 5, and preferably at least 6. That pH is usually at most 9, preferably at most 8.

In a first embodiment, the manufacturing procedure usually involves the mixing of the amine, epichlorohydrin and water, followed by heating at the desired temperature for the desired duration. The aqueous solution is further concentrated by vacuum distillation. The temperature of distillation is as described for the reaction. The distillation pressure is usually lower than or equal to 100 mbar absolute, preferably lower than or equal to 75 mbar and most preferably lower than or equal to 50 mbar. That pressure is usually higher than or equal to 1 mbar absolute.

In a second embodiment, an aqueous solution of the amine is first added to hydrochloric acid until a pH between 8 and 9 is obtained. Epichlorohydrin is further added to the resulting solution and the mixture stirred at the desired temperature for the desired duration. The solution is further distilled under vacuum to the solid 3-chloro-2-trialkylammonium chloride. The solid can be used as such or further cyclized into the glycidyl derivative by reaction with sodium hydroxide in aqueous solution.

In a third embodiment, an amine hydrochloride is dispersed in water. Sufficient sodium hydroxide is added to raise de pH from around 3 to around 8. Epichlorohydrin is further added to the resulting solution and the mixture stirred at the desired temperature for the desired duration. The chlorohydrin group is further cyclized into the glycidyl derivative by reaction with sodium hydroxide in aqueous solution.

In the various embodiments, the aqueous solution obtained at the end of the reaction can be further concentrated by vacuum evaporation or distillation at a temperature of less than 50° C. in order to obtain a slurry containing at least 90% by weight of solid, preferably at least 95% by weight. A water miscible alcohol having 3 to 4 carbon atoms, such as isopropanol, n-propanol, and tert-butanol, preferably isopropanol, is added to the slurry, such as to obtain an alcohol content from 10 to 70% wt, preferably from 25 to 50% wt, based on the total weight of the resulting alcohol-water slurry. The precipitated solids are then recovered by filtration or by other means suitable for removing solids from liquid. The solid may optionally be washed with additional volumes of alcohol or another non-solvent and/or dried to remove any trace of water and alcohol.

The reaction product can be recovered as an aqueous solution, or a solid after further treatments, e.g. distillation of the solvents under vacuum, treatment of the solution with an acid or a base.

4.4. Uses

Cationization agents are mainly used in the cationization of starch to be utilized by the paper industry for processing of high quality paper grades or for cationization of textile for dye fixing.

5. FLAME RETARDANTS

5.1. General

The product containing epichlorohydrin according to the invention can be used for the manufacture of flame retardants additives.

The product containing epichlorohydrin according to the invention can preferably be used for the manufacture of phosphorus containing flame retardants additives.

By phosphorus containing flame retardants, one intends to denote a compound, the chemical formula of which contains at least one phosphorus atom and at least one group selected from 2,3-epoxypropyloxy, 3-chloro-2-hydroxypropyl, and the combination of at least two of them.

Figure 7:
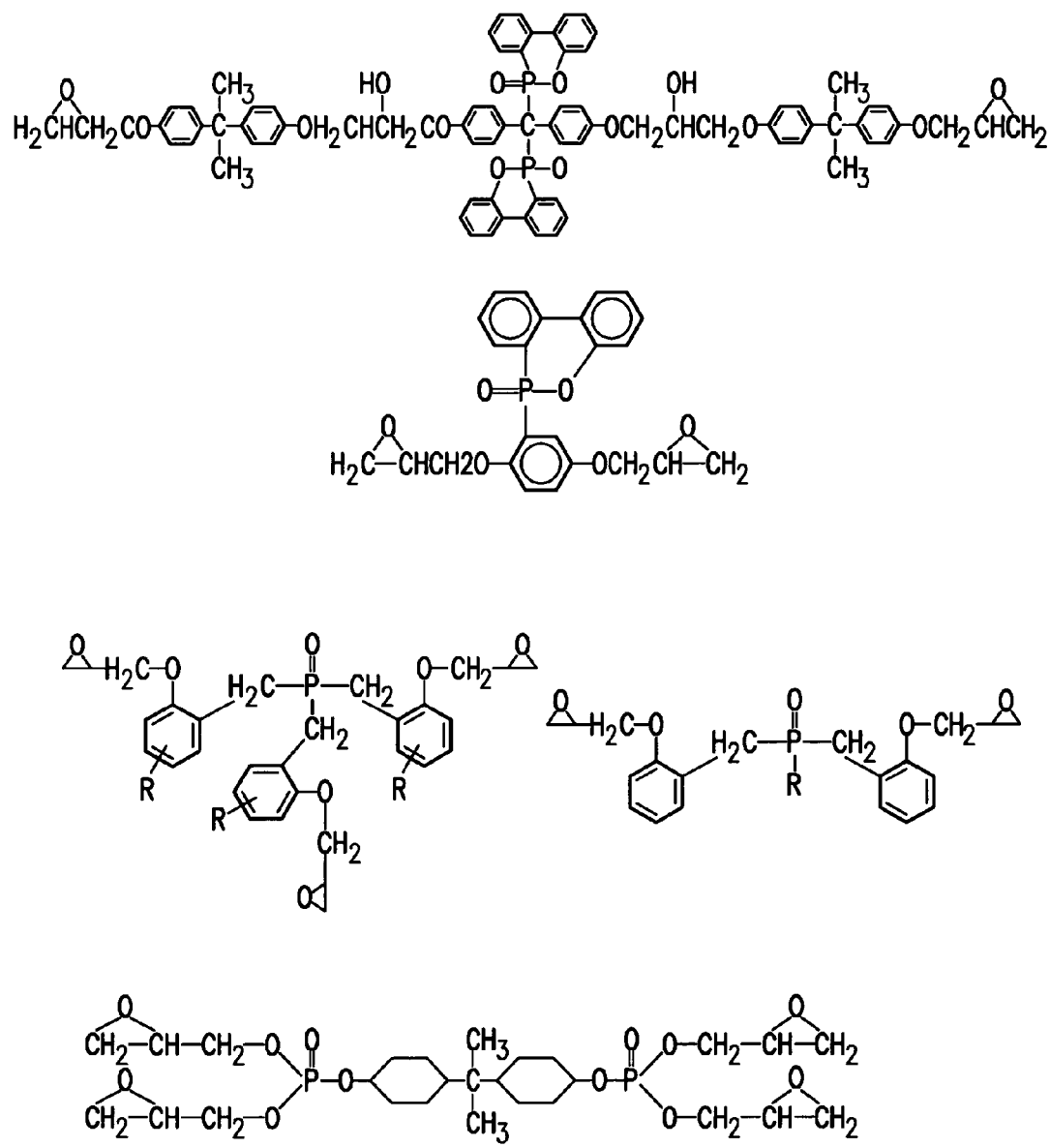
FIG. 7: example of chemical formula of compounds used as phosphorus containing flame retardants.

Examples of chemical formulas for such compounds are presented in FIG. 7.

5.2. Co-Reactants

In the application according to the invention, the product containing epichlorohydrin is usually subjected to a reaction with an inorganic or organic compound containing phosphorus. Such inorganic compounds are for instance a phosphoric acid (ortho, pyro and polyphosphoric acid), a phosphoric acid salt and a phosphorus oxychloride. Examples of organic compounds containing phosphorus are for instance phosphoric acid esters (of ortho, pyro and polyphosphoric acid), phosphonic acids, their esters or their salts, phosphinic acids, their esters or their salts and phosphine oxides.

The compounds containing phosphorus may be represented by the general formula

or

wherein X', $X^2$, $X^3$ can independently be selected from a halogen, H, OH, $OR^{41}$, $R^{41}$, $OR^{42}(OH)_n$ and $R^{42}(OH)_n$ wherein the halogen is preferably selected from bromine and chlorine and is preferably chlorine wherein $R^{41}$ is an alkyl, an aryl, an alkylaryl, an arylalkyl, a cycloalkyl radical containing from 1 to 20 carbon atoms, often from 3 to 12 carbon atoms wherein $R^{42}$ is an alkylene, arylene, alkylarylene, arylalkylene, cycloalkylene radical containing from 1 to 20 carbon atoms, often from 3 to 12 carbon atoms wherein n is an integer equal to 1 or 2 wherein at least two of $X^1$, $X^2$, $X^3$ can be joined to form a ring, preferably with the phosphorus atom.

Examples of phosphorus containing compounds are tris(1,3-dichloro-2-propyl) phosphate, tris(1-chloro-2-propyl) phosphate, tris(2,3-dichloropropyl) phosphate, isobutylbis (hydroxypropyl)phosphine oxide, 10-(2',5'-dihydroxyphenyl)-9,10-dihydro-9-oxa-10-phosphaphenanthrene-10-oxide (DHQEP), 9,10-dihydro-9-oxa-10-phosphaphenanthrene-10-oxide (DOPO), the reaction products of DOPO and 4,4'-dihydroxybenzophenone (DOPO2OH and 2DOPO-PhOH,II as represented in Liu Y. L., Journal of Polymer Science: Part A: Polymer Chemistry, 2002, Vol. 40, 359-368 and Journal of Applied Polymer Science, 2002, Vol. 83, 1697-1701).

5.3. Processes

The reaction between the product containing epichlorohydrin and the phosphorus containing compound is carried out by any process known in the art such as those described in Journal of Applied Polymer Science, 2002, Vol. 83, 1697-1701).

The reaction is generally carried out in the liquid phase, possibly in the presence of a solvent. The solvent may be selected from water, an organic solvent e.g. an alcohol, or mixtures thereof. An alcohol is preferred. Monoalcohols, like methanol, ethanol, n-propanol, isopropanol and butanol are preferred organic solvents, with ethanol being particularly preferred.

The content of epichlorohydrin in the reaction mixture is usually higher than or equal to 0.1 mol/l, often higher than or equal to 1.0 mol/l, frequently higher than or equal to 2 mol/l and particularly higher than or equal to 5 mol/l. That epichlorohydrin content is usually lower than 20 mol/l.

The content of the phosphorus containing compound in the reaction mixture is usually higher than or equal to 0.1 mol/l, often higher than or equal to 0.2 mol/l and frequently higher than or equal to 0.5 mol/l. That content is usually lower than 2 mol/l.

The molar epichlorohydrin/phosphorus containing compound ratio is usually higher than or equal to 1, preferably higher than or equal to 2, more preferably higher than or equal to 5 and most preferably higher than or equal to 10. That ratio is usually lower than or equal to 50, more preferably lower than or equal to 30 and most preferably lower than or equal to 20.

The temperature at which the reaction is carried out is generally higher than or equal to 0° C., often higher than or equal to 5° C., frequently higher than or equal to 10° C., particularly higher than or equal to 20° C. and more specifically higher than or equal to 50° C. That temperature is usually lower than or equal to 100° C., preferably lower than or equal to 80° C., more preferably lower than or equal to 60° C., and most preferably lower than or equal to 30° C.

The pressure at which the reaction is carried out is generally higher than or equal to 0.1 bar absolute, preferably higher than or equal to 0.2 bar, more preferably higher than or equal to 0.5 bar and most preferably higher than or equal to 1 bar. That pressure is usually lower than or equal to 20 bar, preferably lower than or equal to 10 bar, more preferably lower than or equal to 5 bar, and most preferably lower than or equal to 2 bar.

The duration of the reaction depends on the temperature at which the reaction is carried out. That duration is generally higher than or equal to 10 min absolute, preferably higher than or equal to 1 h, more preferably higher than or equal to 10 min and most preferably higher than or equal to 24 h. That duration is usually lower than or equal to 72 h, preferably lower than or equal to 60 h, more preferably lower than or equal to 48 h, and most preferably lower than or equal to 30 h.

A basic compound, e.g., potassium hydroxide can be present in the reaction medium. This is generally the case when the phosphorus containing compound includes OH groups in the molecule. The molar basic compound/phosphorus containing compound ratio is usually higher than or equal to 0.1, preferably higher than or equal to 0.15, and most preferably higher than or equal to 0.2. That ratio is usually lower than or equal to 5, more preferably lower than or equal to 3 and lost preferably lower than or equal to 1.

An onium salt, preferably a quaternary ammonium or phosphonium salt, more preferably a quaternary ammonium chloride, like for instance benzyltrimethylammonium chloride, can be present in the reaction medium. This is generally the case when the phosphorus containing compound is a phosphine oxide. The onium/phosphorus containing compound ratio is usually higher than or equal to 0.01, preferably higher than or equal to 0.05, and most preferably higher than or equal to 0.1. That ratio is usually lower than or equal to 1, more preferably lower than or equal to 0.5 and most preferably lower than or equal to 0.2.

The product of the reaction can be recovered by any means, e.g., filtration and submitted to washing operations before being submitted to evaporation under reduced pressure.

5.4. Uses

Flame retardants are usually used to inhibit the evolution of combustible gases in various materials such as polymers, in particular in polyurethane foams.

6. DETERGENT INGREDIENTS

6.1. General

The product containing epichlorohydrin according to the invention can be used for the manufacture of detergent ingredients. By detergent ingredient, one intends to denote a compound, the chemical formula of which contains at least one 3-sulfonate-2-hydroxy-propyloxy group. The compound can be an oligomer or a polymer. An oligomer is a polymer with a number of repeat units in each polymer molecule of less than 20.

By detergent ingredient, one intends to denote a polymer, at least one repeat unit of which comprises at least one 2-hydroxypropylammonium group, preferably a 2-hydroxypropylimidazolidium group.

The product containing epichlorohydrin according to the invention can preferably be used for the manufacture of cationic monomers, polymers or oligomers, anionic surfactants, for instance sulfonates based surfactants, preferably alkyl glyceryl ether sulfonate surfactants, monomeric or oligomeric or cationic cyclic amine based polymers.

6.2. Co-Reactants

In the application according to the invention, when the detergent auxiliary is a sulfonate based surfactant, the product containing epichlorohydrin is usually subjected to a reaction with an aliphatic alcohol containing from 10 to 40 carbon atoms, preferably from 10 to 22 carbon atoms more preferably from 14 to 18 carbon atoms and most preferably from 16 to 18 carbon atoms. The alkyl chain may be branched or linear or ethoxylated, wherein when present, the branches comprise an alkyl moiety containing from 1 to 4 carbon atoms, such as methyl or ethyl.

In the application according to the invention, when the detergent ingredient is a cationic amine based polymer, the product containing epichlorohydrin is usually subjected to a reaction with an amine selected from the group consisting of linear alkylamines, branched alkylamines, cyclo alkylamines, alkoxyamines, amino alcohols, cyclic amines containing at least one nitrogen atom in a ring structure, alkylenediamines, polyetherdiamines, polyalkylenepolyaminesamine.

Specific examples of the said amines are given above.

Cyclic amines containing at least one nitrogen atom in a ring structure are for example monoaminoalkylpiperazines, bis(aminoalkyl)piperazines, monoaminoalkylimidazoles, aminoalkylmorpholines, aminoalkylpiperidines and aminoalkylpyrrolidines. The monoaminoalkylpiperazines are for example 1-(2-aminoethyl)piperazine and 1-(3-aminopropyl)piperazine. Preferred monoaminoalkylimidazoles have 2 to 8 carbon atoms in the alkyl group. Examples of suitable compounds are 1-(2-aminoethyl)imidazole and 1-(3-aminopropyl)imidazo le. Suitable bis(aminoalkyl)piperazines are for example 1,4-bis(2-aminoethyl)piperazine and 1,4-bis(3-aminopropyl)-piperazine. Preferred amino alkylmorpholines are aminoethylmorpholine and 4-(3-aminopropyl)-morpholine. Other preferred compounds of this group are aminoethylpiperidine, aminopropylpiperidine and aminopropylpyrrolidine.

Cyclic amines with at least two reactive nitrogen atoms in the ring are for example imidazole, C-alkyl substituted imidazoles having 1 to 25 carbon atoms in the alkyl group such as 2-methylimidazole, 2-ethylimidazole, 2-propylimidazole, 2-isopropylimidazole and 2-isobutylimidazole, imidazoline, C-alkyl substituted imidazo lines having 1 to 25 carbon atoms in the alkyl group and arylimidazo lines such as 2-phenylimidazo line and 2-tolylimidazo line, piperazine, N-alkylpiperazines having 1 to 25 carbon atoms in the alkyl group such as 1-ethylpiperazine, 1-(2-hydroxy-1-ethyl)piperazine, 1-(2-hydroxy-1-propyl)piperazine, 1-(2-hydroxy-1-butyl)piperazine, 1-(2-hydroxy-1-pentyl)piperazine, 1-(2,3-dihydroxy-1-propyl)piperazine, 1-(2-hydroxy-3-phenoxyethyl)piperazine, 1-(2-hydroxy-2-phenyl-1-ethyl)piperazine, N,N'-dialkylpiperazines having 1 to 25 carbon atoms in the alkyl group for example 1,4-dimethylpiperazine, 1,4-diethylpiperazine, 1,4-dipropylpiperazine, 1,4-dibenzylpiperazine, 1,4-bis(2-hydroxy-1-ethyl)piperazine, 1,4-bis(2-hydroxy-1-propyl)piperazine, 1,4-bis(2-hydroxy-1-butyl) piperazine, 1,4-bis(2-hydroxy-1-pentyl)piperazine, and 1,4-bis(2-hydroxy-2-phenyl-1-ethyl)piperazine. Other cyclic amines with at least two reactive nitrogen atoms are melamine and benzimidazoles such as 2-hydroxybenzimidazole and 2-aminobenzimidazole.

6.3. Processes

The reaction between the product containing epichlorohydrin and the alcohol is carried out by any process known in the art such as those described in U.S. Pat. No. 5,567,359 and US 2006/0079433, the contents of which are incorporated herein by reference.

The reaction is usually carried out at a temperature between 65 and 90° C.

Typical molar ratios of alcohol:epichlorohydrin range from 1:1.24 to 1:4.02.

A catalyst is usually used when carrying out the reaction, for instance stannic chloride. The mass ratio of initial alcohol: stannic chloride is generally of 100:0.67.

The duration of the reaction is usually between 0.25 and 1 h.

The epichlorohydrin/alcohol ratio and the duration can be adapted to the required degree of oligomerisation Epichlorhydrin is usually slowly added to the alcohol-catalyst mixture.

The product of the reaction is a monomeric or oligomeric alkyl chloroglyceryl ether.

The alkyl chloroglyceryl ether is further converted into an alkyl glycidyl ether by reaction with a basic compound, preferably sodium hydroxide. That reaction is usually carried out with a 35% aqueous solution of sodium hydroxide at a temperature higher than 90° C. and for a molar ratio alcohol:NaOH of 1:1.5.

The alkyl glycidyl ether is further converted into an alkyl glyceryl surfactant by reaction usually with a mixture of sodium bisulfite and sodium sulfite, generally obtained by combining sodium meta-bisulfite with sodium hydroxide.

The reaction between the product containing epichlorohydrin and the amine is carried out by any process known in the art such as those described in U.S. Pat. No. 6,740,633 and US 2006/0052272, the contents of which are incorporated herein by reference.

The reaction is usually carried out at a temperature between 25 and 90° C., in two steps the first one at a temperature between 40 and 60° C. and the second one between 90 and 100° C.

Typical molar ratios of amine:epichlorohydrin range from 1:1 to 1:1.4.

The duration of the reaction is usually between 0.25 and 1 h.

The condensation product between the amine and epichlorohydrin is usually further quaternarized using alkyl halides, epoxides, chloroacetic acid, 2-chloroethanesulfonic acid, chloropropionic acid, epoxysuccinic acid, propane sulfone, 3-chloro-2-hydroxypropanesulfonic acid, dimethyl sulfate and/or diethyl sulfate, or oxidized by oxidation of the tertiary nitrogen atoms of the condensation products to N-oxides.

6.4. Uses

Examples of detergent ingredients are surfactants or surface deposition enhancing materials. They are usually used as components of cleaning compositions for instance dishwashing, laundry compositions, shampoos and synbars.

7. EPICHLOROHYDRIN ELASTOMERS

7.1. General

The product containing epichlorohydrin according to the invention can be used for the manufacture of epichlorohydrin elastomers.

By epichlorohydrin elastomer, one intends to denote a polymer, containing at least one type of repeat units, at least one type of repeat units containing at least one 2-chloromethylethoxy group. The polymer can a homopolymer or a copolymer.

Examples of epichlorohydrin elastomers are homopolymers of epichlorohydrin, copolymers of epichlorohydrin with an alkylene or phenylene oxide, and terpolymers of epichlorohydrin with an alkylene or phenylene oxide, and a glycidyl ether.

The alkylene oxide can be selected from styrene oxide, propylene oxide, ethylene oxide, butene-1 oxide, dodecene-1-oxide, and is preferably ethylene oxide.

The glycidyl ether can be selected from alkyl and haloalkyl glycidyl ethers, for instance, 2-chloroethyl glycidyl ether and allyl glycidyl ether.

7.2. Co-Reactants

In the application according to the invention, the product containing epichlorohydrin is usually subjected to a reaction with an alkylene or phenylene oxide or with an alkylene or phenylene oxide and a glycidyl ether or the epichlorohydrin is homopolymerized.

7.3. Processes

The reaction is carried out by any process known in the art such as those described in U.S. Pat. No. 3,135,705, U.S. Pat. No. 3,158,580, U.S. Pat. No. 3,158,581, U.S. Pat. No. 3,026,270 and U.S. Pat. No. 3,341,491, the contents of which are incorporated herein by reference.

The reaction is usually carried out in solution in aliphatic or aromatic hydrocarbons, chlorinated hydrocarbons, or ether.

The weight ratio between epichlorhydrin and the alkylene oxide is usually between 20:80 and 90:10.

The reaction is preferably carried out in the presence of a catalyst formed by reacting $R^{51}{}_3Al$ and water (thought to be $R^{51}{}_2Al-O-AlR^{51}{}_2$), where $R^{51}$ can be selected from alkyl, cycloalkylaryl or alkaryl radical. The catalyst activity can be improved by the addition of acetylacetone. Some combinations of organozinc and organomagnesium compounds, as well as other additives and chelating agents in combination with alkylaluminum compounds, are also effective catalysts.

The reaction can be carried out in a continuous process using a back-mixed reactor.

The temperature at which the reaction can be carried out is usually comprised between −80° C. and 250° C., preferably between −80 and 150° C., more preferably between −30 and 100° C. A temperature between 25 and 50° C. is particularly convenient The homopolymer of epichlorohydrin and the copolymers can be further cross-linked, e.g., by further reacting with a polyamine, or an amine in the presence of at least one agent from the group of sulfur, dithiocarbamates, thiuram sulfides and thiazoles, or with a metal compound selected from the group consisting of salts of aromatic carboxylic acids, aliphatic carboxylic acids, carbonic acid, phosphorous acid, silicic acid, and oxides of the metals of Groups IIA, IIB and IVA of the periodic Table and at least one heterocyclic compound selected from the group consisting of 2-mercaptoimidazolines and 2-mercaptopyrimidine.

7.4. Uses

The epichlorohydrin elastomers are generally used in specialty applications, like for instance automotive components (fuel pump diaphragms, emission control hoses, motor mounts, gaskets, seals and portable fuel tanks), in the aircraft industry, for specialty roofing membranes, coated fabrics, solvent storage containers, paper mill and printing roll and in a variety of oil specialties.

EXAMPLES

Five epichlorohydrin (ECH) samples have been used. Their compositions obtained by gas chromatography analysis are presented in Table 1.

TABLE 1

| Component (g/kg) | ECH 1 | ECH 2 | ECH3 | ECH4 | ECH5 |
|---|---|---|---|---|---|
| acetaldehyde | 0.004 | n.d | n.d | n.d. | n.d. |
| acrolein | <0.001 | 0.003 | 0.003 | n.d. | n.d. |
| 2-propanol | <0.001 | n.d. | n.d. | n.d. | n.d. |
| 3-chloro-1-propene | n.d. | n.d. | n.d. | n.d. | n.d. |
| allyl alcohol | 0.001 | <0.001 | <0.001 | n.d. | 0.003 |
| hydroxyacetone | 0.094 | 0.018 | 0.018 | 0.006 | 0.006 |
| chloroacetone + (3,3-dichloro-1-propene) | 0.033 | 0.038 | 0.040 | n.d. | 0.024 |
| 1,2-dichloropropane | 0.042 | n.d. | n.d. | 0.001 | n.d. |
| 2,3-dichloro-1-propene | 0.005 | n.d. | n.d. | 0.004 | n.d. |
| 1-chloro-2,3-epoxypropane(*) | >998.464 | >999.474 | >999.045 | >999.503 | >999.865 |
| 1,3-dichloro-1-propene cis maj. + (C6H14O min.) | 0.219 | 0.008 | 0.008 | 0.032 | 0.004 |
| 2-chloro-2-propene-1-ol | 0.348 | 0.016 | 0.016 | 0.14 | 0.012 |
| 1,3-dichloro-1-propene trans | 0.035 | 0.010 | 0.010 | 0.008 | 0.009 |
| $C_5H_{10}O/C_4H_7ClO$ | n.d. | n.d. | n.d. | 0.014 | 0.001 |
| $C_6H_{12}O$ | n.d. | n.d. | n.d. | 0.011 | <0.001 |
| 1,3-dichloropropane | 0.002 | 0.34 | 0.34 | 0.005 | 0.030 |
| Cyclopentanone | 0.001 | 0.004 | 0.004 | n.d. | 0.004 |
| dibromochloromethane | 0.004 | n.d. | n.d. | 0.084 | n.d. |
| $C_6H_{10}O$ iso 1 | 0.003 | n.d. | n.d. | 0.009 | <0.001 |
| $C_6H_{10}O$ iso 2 | 0.012 | n.d. | n.d. | 0.009 | 0.001 |
| 1,2-epoxyhexane + (1,2,2-trichloropropane) | 0.030 | 0.002 | 0.002 | n.d. | 0.001 |
| $C_6H_{10}O$ iso 3 | 0.004 | n.d. | n.d. | 0.031 | 0.001 |
| dichloroepoxypropane | 0.003 | n.d. | n.d. | 0.006 | n.d. |
| 1,3,3-trichloro-1-propene cis + 1,1,3-trichloropropene | 0.012 | n.d. | n.d. | 0.004 | n.d. |
| 1,1,2-trichloropropane | 0.211 | 0.001 | 0.001 | 0.025 | 0.007 |
| chlorobenzene | 0.011 | <0.001 | <0.001 | 0.001 | 0.007 |
| 1,3,3-trichloro-1-propene trans | 0.015 | n.d. | n.d. | 0.012 | 0.001 |
| 1,2,3-trichloropropene trans | 0.016 | <0.001 | <0.001 | 0.003 | 0.001 |
| 1,3-dichloro-2-propanol | 0.111 | 0.023 | 0.024 | 0.017 | 0.008 |
| 1,2,3-trichloropropane | 0.014 | n.d. | n.d. | 0.024 | n.d. |
| 1,2,3-trichloropropene cis | 0.002 | n.d. | n.d. | n.d. | n.d. |
| 3-chloro-1,2-propanediol + 2,3-dichloro-1-propanol | 0.13 | <0.001 | 0.001 | n.d. | 0.001 |
| $C_6H_{13}Br$ | n.d. | n.d. | n.d. | 0.005 | n.d. |
| $C_6H_{10}Cl_2$ iso 1 | n.d. | n.d. | n.d. | 0.005 | n.d. |
| $C_6H_{10}Cl_2$ iso 2 | n.d. | n.d. | n.d. | 0.004 | n.d. |
| methyl glycidyl ether | 0.007 | 0.054 | 0.48 | n.m. | n.m. |
| Unknowns (sum) | 0.170 | 0.007 | 0.008 | 0.087 | 0.024 | n.d.: not detected,
n.m.: not measured
(*)1-chloro-2,3-epoxypropane amount calculated on the basis of the total content of other organic components

Examples 1 to 10

Homopolymerization of ECH

The tests have been carried out according to the following procedure with epichlorohydrin sample ECH1 (examples 1 to 3), ECH 2 (examples 4 to 6) and ECH 3 (examples 7 to 10). The quantities of chemicals are indicated in Table 2.

The polymerization of epichlorohydrin (ECH) has been carried out in the presence of the system tetraoctylammonium bromide($Noct_4Br$)/triisobutyl aluminium (TiBA).

The epichlorohydrin has been dried over calcium hydride under vacuum for 24 h at 25° C. and further distilled.

The polymerization reactions have been carried out in pyrex vessels fitted with polytetrafluorethylene valves. The vessels have been evacuated under flame heating to remove residual moisture. After cooling to room temperature, the vessels have been cooled to −30° C. (ethanol/liquid nitrogen cooling bath) and toluene and epichlorohydrin, have been added under vacuum. After those additions, argon has been introduced in the vessel and tetraoctylammonium bromide and triisobutyl aluminium have been added to the vessel. This addition constituted the time zero of the reaction. After a given time under magnetic stirring at −30° C., the reaction has been stopped by adding 1-2 ml of ethanol to the vessel. Half of the volume of the reaction medium has then been submitted to evaporation after which the polymer has been recovered from the vessel.

The conversion has been obtained by comparing the weight of recovered polymer with the weight of added epichlorohydrin.

The theoretical molar weight (Mn th.) has been calculated on the basis of the quantity of tetraoctylammonium bromide.

The measured polymer molar weight (Mn exp) and the molar weight dispersion have been obtained by Gel Permeation Chromatography.

The tacticity of the polymer has been obtained by $^{13}C$ and $^{1}H$ NMR.

The results of the tests are summarized in Table 3.

TABLE 2

| Example n° | ECH (ml) | Toluene (ml) | $Noct_4Br$ (ml) | TiBA (ml) |
|---|---|---|---|---|
| 1 | 4 | 10.2 | 2.15 | 0.71 |
| 2 | 4 | 10.2 | 2.15 | 0.71 |
| 3 | 3.4 | 9.9 | 0.91 | 0.30 |
| 4 | 4 | 10.2 | 2.15 | 0.71 |
| 5 | 4 | 10.2 | 2.15 | 0.71 |
| 6 | 4 | 11.6 | 1.08 | 0.35 |
| 7 | 4 | 10.2 | 2.15 | 0.71 |
| 8 | 4 | 10.2 | 2.15 | 0.71 |
| 9 | 3.6 | 11.4 | 0.97 | 0.43 |
| 10 | 4 | 11.6 | 1.08 | 0.35 |

TABLE 3

| Example | Reaction time (h) | Conversion (mol %) | Mn th. (g/mol) | Mn exp. (g/mol) | Dispersion | Tacticity |
|---|---|---|---|---|---|---|
| 1 | 1 | 100 | 10000 | 10700 | 1.17 | atactic |
| 2 | 1 | 100 | 10000 | 10100 | 1.23 | n.m. |
| 3 | 2 | 100 | 20000 | 20200 | 1.17 | n.m. |
| 4 | 1 | 100 | 10000 | 16400 | 1.22 | n.m. |
| 5 | 1 | 100 | 10000 | 11200 | 1.20 | atactic |
| 6 | 1 | 100 | 20000 | 77700 (20%) | 1.40 | n.m. |
|   |   |   |   | 22200 (80%) | 1.20 |   |
| 7 | 1 | 80 | 8000 | 6800 | 1.17 | n.m. |
| 8 | 2 | 95 | 9500 | 12100 | 1.17 | atactic |
| 9 | 2 | 90 | 18000 | 24700 | 1.18 | n.m. |
| 10 | 6 | 94 | 18800 | 17650 | 1.17 | n.m. | n.m.: not measured

Examples 13 to 15

Homopolymerization of ECH

The tests have been carried out according to the following procedure with epichlorohydrin sample ECH1 (example 13), ECH 2 (example 14) and ECH 3 (example 15). The quantities of chemicals are indicated in Table 4.

The polymerization of epichlorohydrin (ECH) has been carried out in the presence of the system water/triethyl aluminium (TEA).

The procedure of example 1 has been followed except that TEA in solution in toluene and water have been added under argon to the vessel first evacuated and dried, left under magnetic stirring under vacuum for 30 min, before ECH in toluene has been added (time zero of the reaction). The polymerization has been carried out at a temperature of 25° C. for 12 h. The results have been summarized in Table 5

TABLE 4

| Example n° | ECH (ml) | Toluene (ml) | $H_2O$ (μl) | TEA (ml) |
|---|---|---|---|---|
| 13 | 4 | 10 | 23 | 0.67 |
| 14 | 4 | 10 | 23 | 0.67 |
| 15 | 4 | 10 | 23 | 0.67 |

TABLE 5

| Example | Reaction time (h) | Conversion (mol %) | Mn exp. (g/mol) | Dispersion | Tacticity |
|---|---|---|---|---|---|
| 13 | 12 | 47 | 216000 | 2.02 | n.m. |
|   |   |   | 7000 | 1.04 |   |
| 14 | 12 | 50 | 285200 | 3.51 | atactic |
|   |   |   | 5850 | 1.08 |   |
| 15 | 12 | 55 | 357600 | 3.45 | atactic |
|   |   |   | 8100 | 1.31 |   | n.m.: not measured

Example 16

Preparation of a Product Consisting Predominantly in Diglycidyl Diether of Bisphenol A According to U.S. Pat. No. 2,811,227

The apparatus employed was a thermostatised flask equipped with a mechanical stirrer, with a jacket containing a thermocouple and with a Dean-Stark separator surmounted by a water-cooled condenser. A pump was used to inject a caustic soda aqueous solution at a constant rate in the flask.

The reaction flask was initially charged with a mixture of bisphenol A (68.4 g, 0.3 mol) and the epichlorohydrin sample ECH$_4$ coming from a propylene-chlorine plant (277.5 g, 3.0 mol). The analysis of the epichlorydrin is given in Table 1. The trichloropropane content is of 0.049 g/kg. The mixture was heated at reflux under stirring to a temperature of 111° C. A 40% aqueous solution of caustic soda (60.8 g, 0.6 mol) was introduced at a rate of 12 ml/h during 3.5 hour. The temperature of the mixture in the flask was maintained in the range 100° C.-115° C. in order to assure a constant reflux. The epichlorohydrin rich organic phase decanted during the reaction as a lower phase in the separator was recycled regularly in the reaction flask and the aqueous rich phase collected as an upper phase in the separator was regularly drawn off. The heating was maintained for 15 min after the total introduction of the caustic soda solution to achieve the collect of the water phase in the decantor. 29.7 g of aqueous phase was collected with a composition given in Table 6.

The epichlorohydrin in excess was removed from the reaction mixture by distillation under a vacuum of 30 mbar and by a progressive heating of the mixture to 109° C. 156.1 g (1.7 mol) of epichlorohydrin was recovered in this step. The composition of the distillate is given in Table 6.

The salt was separated from the crude product (45.5 g) after addition of 567.2 g of toluene under agitation and by filtration. The cake of filtration was washed with 124.4 g of toluene. The toluene solutions were mixed and evaporated at 185° C. under a pressure of 1 mbar.

659.4 g of toluene was recovered as the condensate of the evaporated fraction with a composition given in Table 6. The residual product of the evaporation (100.5 g) contained the diglycidyl ether of bis-phenol A as a major product and no trace of unconverted bis-phenol A (<5 mg/kg). The residue contained 4.98 mol epoxy per kg and 1.52% of hydrolysable chlorine.

Example 17

The trial was realized in the apparatus described in example 16.

The reaction flask was initially charged with a mixture of bisphenol A (68.4 g, 0.3 mol) and epichlorohydrin sample ECH 5 (277.5 g, 3.0 mol). The analysis of the epichlorydrin is given in Table 1. The trichloropropane content is of 0.007 g/kg. The mixture was heated at reflux under stirring to a temperature of 119° C. A 40% aqueous solution of caustic soda (60.8 g, 0.6 mol) was introduced at a rate of 12 ml/h during 3.5 hour. The temperature of the mixture in the flask was maintained in the range 102° C.-119° C. in order to assure a constant reflux. The epichlorohydrin rich organic phase decanted during the reaction as a lower phase in the separator was recycled regularly in the reaction flask and the aqueous rich phase collected as an upper phase in the separator was regularly drawn off. The heating was maintained for 15 min after the total introduction of the caustic soda solution to achieve the collect of the water phase in the decantor. 54.5 g of aqueous phase was collected with a composition given in Table 6.

The epichlorohydrin in excess was removed from the reaction mixture by distillation under a vacuum of 30 mbar and by a progressive heating of the mixture to 118° C. 148.2 g (1.5 mol) of epichlorohydrin was recovered in this step. The composition of the distillate is given in Table 6.

The salt was separated from the crude product (47.8 g) after addition of 228.4 g of toluene under agitation and by filtration. The cake of filtration was washed with 97.3 g of toluene. The toluene solutions were mixed and evaporated at 180° C. under a pressure of 1 mbar.

305.0 g of toluene was recovered as the condensate of the evaporation with a composition given in Table 6. The residual product of the evaporation (99.8 g) contained the diglycidyl ether of bis-phenol A as a major product and no trace of unconverted bis-phenol A (<5 mg/kg). The residue contained 4.93 mol epoxy per kg and 0.49% of hydrolysable chlorine.

The High Performance Liquid Chromatography analyses of the residual products obtained in examples 16 and 17 are similar.

TABLE 6

| | Example 16 | | | Example 17 | | |
| --- | --- | --- | --- | --- | --- | --- |
| Component | Epichlorohydrin evaporated (g/kg) | Water evaporated (mg/l) | Toluene evaporated (g/kg) | Epichlorohydrin evaporated (g/kg) | Water evaporated (mg/l) | Toluene evaporated (g/kg) |
| acetaldehyde | n.d. | 2.9 | n.d. | n.d. | 1.3 | n.d. |
| acrolein | n.d. | 0.58 | n.d. | 0.002 | 0.42 | n.d. |
| 2-propanol | n.d. | <0.05 | n.d. | n.d. | 0.3 | n.d. |
| 3-chloro-1-propene | 0.001 | n.d. | n.d. | n.d. | n.d. | n.d. |
| allyl alcohol | n.d. | n.d. | n.d. | 0.001 | 0.2 | n.d. |
| hydroxyacetone | 0.016 | n.d. | n.d. | 0.002 | n.d. | n.d. |
| chloroacetone + (3,3-dichloro-1-propene) | 0.003 | 0.65 | n.d. | 0.002 | 0.53 | n.d. |
| 1,2-dichloropropane | | | n.d. | n.d. | n.d. | n.d. |
| 2,3-dichloro-1-propene | 0.005 | 0.07 | n.d. | n.d. | n.d. | n.d. |
| 1-chloro-2,3-epoxypropane | principal product | (45 g/kg) | 1.6 | principal product | (46 g/kg) | 3.3 |
| 1,3-dichloro-1-propene cis maj. + (C6H14O min.) | 0.026 | 0.36 | n.d. | 0.003 | n.d. | n.d. |
| 2-chloro-2-propene-1-ol | 0.19 | 0.12 | n.d. | 0.016 | <0.05 | n.d. |
| 1,3-dichloro-1-propene trans | 0.007 | <0.05 | n.d. | 0.008 | n.d. | n.d. |
| C$_5$H$_{10}$O/C$_4$H$_7$ClO | 0.019 | 0.05 | n.d. | 0.001 | n.d. | n.d. |
| C$_6$H$_{12}$O | 0.022 | 0.28 | n.d. | 0.021 | n.d. | n.d. |
| 1,3-dichloropropane | 0.001 | n.d. | n.d. | 0.03 | <0.05 | n.d. |
| Cyclopentanone | n.d. | n.d. | n.d. | 0.006 | n.d. | n.d. |
| dibromochloromethane | 0.080 | n.d. | n.d. | n.d. | n.d. | n.d. |
| C$_6$H$_{10}$O iso 1 | 0.033 | 0.11 | n.d. | 0.038 | n.d. | n.d. |
| C$_6$H$_{10}$O iso 2 | 0.040 | 0.31 | n.d. | 0.001 | n.d. | n.d. |
| 1,2-epoxyhexane + (1,2,2-trichloropropane) | n.d. | n.d. | n.d. | 0.001 | n.d. | n.d. |

TABLE 6-continued

|  | Example 16 | | | Example 17 | | |
| --- | --- | --- | --- | --- | --- | --- |
| Component | Epichlorohydrin evaporated (g/kg) | Water evaporated (mg/l) | Toluene evaporated (g/kg) | Epichlorohydrin evaporated (g/kg) | Water evaporated (mg/l) | Toluene evaporated (g/kg) |
| $C_6H_{10}O$ iso 3 | 0.036 | 0.21 | n.d. | 0.002 | n.d. | n.d. |
| dichloroepoxypropane | 0.006 | n.d. | n.d. | n.d. | n.d. | n.d. |
| 1,3,3-trichloro-1-propene cis + 1,1,3-trichloropropene | 0.006 | n.d. | n.d. | n.d. | n.d. | n.d. |
| 1,1,2-trichloropropane | 0.005 | n.d. | n.d. |  | n.d. | n.d. |
| chlorobenzene | 0.001 | n.d. | n.d. | 0.008 | n.d. | n.d. |
| 1,3,3-trichloro-1-propene trans | 0.009 | n.d. | n.d. | n.d. | n.d. | n.d. |
| 1,2,3-trichloropropene trans | 0.003 | n.d. | n.d. | 0.001 | n.d. | n.d. |
| 1,3-dichloro-2-propanol | 3.4 | 143 | 0.38 | 2.5 | 111 | 0.074 |
| 1,2,3-trichloropropane | 0.022 | n.d. | 0.002 | n.d. | n.d. | n.d. |
| 1,2,3-trichloropropene cis | n.d. | n.d. | n.d. | n.d. | n.d. | n.d. |
| 3-chloro-1,2-propanediol + 2,3-dichloro-1-propanol | 0.13 | 5.9 | 0.064 | 0.071 | 4.1 | 0.033 |
| $C_6H_{13}Br$ | n.d. | <0.05 | 0.005 | n.d. | <0.05 |  |
| $C_6H_{10}Cl_2$ iso 1 | 0.009 | n.d. | n.d. | n.d. | n.d. | n.d. |
| $C_6H_{10}Cl_2$ iso 2 | 0.007 | n.d. | n.d. | n.d. | n.d. | n.d. |
| methyl glycidyl ether | n.m. | n.m. | n.m. | n.m. | n.m. | n.m. |
| Unknowns (sum) | 0.299 | 10.00 | 1.31 | 0.213 | 1.3 | 1.373 | n.d.: not detected,
n.m.: not measured

Example 18

A glass thermostated jacketed reactor having a working volume of 305 ml was supplied continuously with 47.2 wt % sodium hydroxide and with an aqueous mixture of dichloropropanol, a mixture prepared from glycerol and concentrated hydrochloric acid in the presence of an organic acid according to the International Application WO 2005/054167 filed by Solvay SA. The mixture contained 575 g of water/kg, 404.6 g of 1,3-dichloro-2-propanol/kg, 20.1 g of 2,3-dichloro-1-propanol/kg, 0.14 g of acrolein/kg, 0.13 g of epichlorohydrin/kg, 0.04 g of 1,2,3-trichloropropane/kg, 0.04 g of chloroacetone/kg and 0.03 g of an ether of crude formula $C_6H_{10}O_2Cl_2$/kg. The sodium hydroxide was introduced at a flow rate of 262 g/h and the aqueous dichloropropanol mixture was introduced at a flow rate of 1180 g/h. The reaction medium was constantly maintained at 25° C. with vigorous stirring. The liquid mixture exiting the reactor by continuous overflow was collected and then separated in batch mode in a glass funnel so as to obtain a first separated fraction and a second separated fraction. 3753 g of first separated fraction (MEL1) were subjected to a batch distillation under a vacuum of 193 mbar. The batch distillation was carried out using a round-bottomed flask equipped with a magnetic stirrer bar, a thermocouple to measure the temperature of the liquid and a plate distillation column surmounted by a device enabling part of the distillate to be refluxed at the top of the column. The glass plate column comprised 5 plates having a diameter of 30 mm, pierced by an internal aperture 10 mm diameter central hole for the flow of liquid and three rows of small holes having a diameter of around 0.8 mm, spaced at regular intervals of less than 1 mm between each hole, placed in an arc over three quarters of the circumference. The spacing between the plates was 30 mm. The column was adiabatic (glass jacket under vacuum). A thermocouple placed in the top of the distillation column enabled the temperature of the gas phase distilled to be measured. The distillate was collected in a funnel with a stopcock. A first distillation fraction was collected between 49° C. and 67° C. and gave, after separation, 425 g of an organic phase (D1 org) and 159 g of an aqueous phase (D1 aq). The organic phase (D1 org) was combined with the contents of the boiler to give the mixture (MEL2) which was then distilled at a temperature of 187° C. A second distillation fraction was collected between 66° C. and 67° C. and resulted, after separation, in 244 g of an organic phase (D2 org) and 11.5 g of an aqueous phase (D2 aq). A main distillate of 2082 g of epichlorohydrin at 999.5 g/kg was then collected (D3) at a temperature of 67° C. The mixture constituting the final boiler (MEL3) weighed 1226 g and only contained a very low fraction of epichlorohydrin implemented. The organic phase D2 org and the boiler MEL3 could be recycled to the distillation operations in order to recover, for enhanced value, epichlorohydrin and a mixture of 1,3-dichloro-2-propanol and 2,3-dichloro-1-propanol respectively. The compositions (g/kg) used and obtained in the distillation operations are described in Table 7.

TABLE 7

|  | MEL1 | D1 org | D1 aq | MEL2 | D2 org | D2 aq | D3 | MEL3 |
| --- | --- | --- | --- | --- | --- | --- | --- | --- |
| Acrolein | 0.2 | 0.61 | 0.13 | 0.076 | 0.99 | 0.12 | 0.050 | 0.006 |
| Acetone | 0.006 | 0.024 | 0.02 | <0.005 | 0.027 | 0.01 | <0.01 | <0.005 |
| Isopropanol | 0.032 | 0.124 | n.d. | 0.014 | 0.15 | n.d. | <0.005 | n.d. |
| 2-Chloropropane | 0.047 | 0.021 | n.d. | <0.005 | 0.012 | n.d. | n.d. | n.d. |
| Allyl alcohol |  | 0.003 | n.d. | n.d. | 0.003 | n.d. | n.d. | n.d. |
| 2,3-Epoxybutane | <0.005 | 0.008 | n.d. | n.d. | 0.010 | n.d. | n.d. | n.d. |
| $C_4H_8O$ | <0.005 | 0.010 | n.d. | n.d. | 0.012 | n.d. | n.d. | n.d. |
| 2-Butanone | <0.005 | 0.003 | n.d. | n.d. | 0.005 | n.d. | n.d. | n.d. |
| Hydroxyacetone | n.d. |  | n.d. | n.d. | 0.001 | n.d. | n.d. | n.d. |
| Chloroethanol | n.d. | 0.005 | n.d. | n.d. | 0.001 | n.d. | n.d. | n.d. |

TABLE 7-continued

| | MEL1 | D1 org | D1 aq | MEL2 | D2 org | D2 aq | D3 | MEL3 |
|---|---|---|---|---|---|---|---|---|
| Chloroacetone | 0.039 | 0.025 | n.d. | 0.039 | 0.034 | 0.03 | 0.05 | 0.019 |
| Epichlorohydrin | 653 | 982 | 46 | 666 | 989 | 36 | 999.5 | 29 |
| Glycidol | 0.06 | 0.000 | n.d. | 0.07 | n.d. | n.d. | n.d. | 0.24 |
| 2-chloro-2-propen-1-ol | <0.005 | 0.005 | 0.16 | <0.005 | 0.008 | 0.04 | <0.01 | 0.005 |
| cis-1,3-Dichloropropene | n.d. | 0.003 | 0.03 | <0.005 | 0.003 | 0.02 | <0.01 | <0.005 |
| trans-1,3-Dichloropropene | n.d. | 0.005 | n.d. | <0.005 | 0.009 | n.d. | <0.01 | <0.005 |
| 1,1,1-Trichloropropane | <0.005 | n.d. | n.d. | <0.005 | n.d. | n.d. | n.d. | 0.002 |
| Cyclopentanone | 0.021 | n.d. | n.d. | 0.023 | n.d. | n.d. | <0.01 | 0.021 |
| 3-Chloro-1-propanol | 0.013 | 0.000 | n.d. | 0.020 | n.d. | n.d. | n.d. | 0.016 |
| cis-1,3,3-Trichloropropene | n.d. | n.d. | n.d. | n.d. | n.d. | n.d. | n.d. | <0.005 |
| $C_4H_7ClO_2$ | n.d. | 0.000 | n.d. | n.d. | n.d. | n.d. | n.d. | <0.005 |
| Ethylbenzene | <0.005 | 0.000 | n.d. | n.d. | n.d. | n.d. | n.d. | <0.005 |
| 1,3-Dichloropropan-2-ol | 251 | 0.364 | 0.27 | 271 | 0.013 | 0.82 | 0.010 | 789 |
| 2-Methyl-2-cyclopenten-1-one | n.d. | n.d. | n.d. | <0.005 | n.d. | n.d. | n.d. | <0.005 |
| 1,2,3-Trichloropropane | 0.16 | n.d. | n.d. | 0.018 | n.d. | n.d. | n.d. | 0.015 |
| 2,3-Dichloro-1-propanol + 3-chloro-1,2-propanediol | 56 | 1.94 | 36.42 | 61 | 0.046 | 21 | n.d. | 174 |
| Phenol | 0.011 | n.d. | n.d. | 0.012 | n.d. | n.d. | n.d. | 0.035 |
| $C_6H_8O_2$ | <0.005 | n.d. | n.d. | <0.005 | n.d. | n.d. | <0.01 | 0.008 |
| $C_6H_{12}OCl_2$ | 0.056 | n.d. | n.d. | 0.060 | n.d. | n.d. | n.d. | 0.051 |
| 3,5-Dimethyl-2-cyclohexen-1-one | 0.011 | n.d. | n.d. | 0.012 | n.d. | n.d. | n.d. | 0.035 |
| $C_6H_9Cl_3O_2$ | 0.031 | n.d. | n.d. | 0.034 | n.d. | n.d. | n.d. | 0.102 |
| 1-Phenoxy-2-propanone | 0.88 | n.d. | n.d. | 0.078 | n.d. | n.d. | n.d. | 1.754 |
| $C_6H_{10}Cl_2O_2$ | 0.076 | 0.002 | n.d. | 0.101 | n.d. | n.d. | n.d. | 0.325 |
| $C_9H_9Cl_3$ | <0.005 | n.d. | n.d. | <0.005 | n.d. | n.d. | n.d. | 0.012 |
| $C_6H_{11}O_2Cl_3$ | 0.74 | n.d. | n.d. | 0.81 | n.d. | n.d. | n.d. | 2.95 |
| $C_9H_{15}O_2Cl_2 + C_9H_{17}O_4Cl_3$ | <0.005 | n.d. | n.d. | <0.005 | n.d. | n.d. | n.d. | 0.56 |
| Sum of unknowns | 0.27 | 0.07 | 0.16 | 0.31 | 0.08 | n.d. | n.d. | 1.07 |
| Methyl glycidyl ether | 0.02 | n.d. | n.d. | 0.03 | 0.03 | n.d. | 0.04 | |
| $H_2O$ | 37 | 14.0 | n.d. | 2.32 | 9.9 | n.d. | 0.32 | 0.33 | n.d. = not detected

The invention claimed is:

1. A product, comprising epichlorohydrin and an alkyl glycidyl ether in a positive amount of less than or equal to 0.08 g/kg of product,
    wherein the content of epichlorohydrin is greater than or equal to 900 g/kg of product, and
    wherein the alkyl glycidyl ether is methyl glycidyl ether.

2. The product according to claim 1, wherein the content of epichlorohydrin is greater than or equal to 950 g/kg of product.

3. The product according to claim 1, obtained by dehydrochlorination of a composition containing dichloropropanol and at least one chloroalkoxypropanol.

4. The product according to claim 3, wherein the chloro alkoxy propanol is selected from the group consisting of 2-chloro-3-alkoxy-propane-1-ol, 1-chloro-3-alkoxy-propane-2-ol, and mixtures thereof.

5. The product according to claim 3, wherein the composition containing dichloropropanol is obtained by hydrochlorination of a compound containing glycerol and at least one glycerol alkyl ether in an amount of less than or equal to 0.6 g/kg of compound.

6. A process for producing the product according to claim 1, comprising:
    (a) reacting a composition comprising glycerol with hydrogen chloride in the presence of a carboxylic acid, in order to obtain a composition comprising dichloropropanol and at least one chloro alkoxy propanol in an amount of less than or equal to 0.1 g/kg of composition
    (b) reacting the composition in (a) with a basic agent in order to obtain said product.

7. The process according to claim 6, further comprising:
    (c) a vegetable fat or oil is reacted with an alcohol to obtain the composition comprising glycerol, under such conditions that ethers of glycerol are formed and are not separated from glycerol,
    (d) the composition comprising glycerol obtained in (c) is further subjected to at least one treatment, optionally under reduced pressure, selected from the group consisting of evaporative concentration, evaporative crystallization, distillation, fractional distillation, stripping, and liquid-liquid extraction, in order to obtain a composition comprising glycerol and at least one glycerol alkyl ether in an amount that is lower than or equal to 0.6 g/kg.

8. The product according to claim 1, wherein the methyl glycidyl ether is present in an amount of less than or equal to 0.06 g/kg of product.

9. The product according to claim 1, wherein the methyl glycidyl ether is present in an amount of less than or equal to 0.04 g/kg of product.

10. The product according to claim 1, wherein the methyl glycidyl ether is present in an amount of less than or equal to 0.01 g/kg of product.

11. The product according to claim 1, further comprising cyclopentanone.

12. The product according to claim 11, comprising cyclopentanone in an amount greater than or equal to 0.1 mg/kg of product and less than or equal to 0.5 g/kg of product.

13. The product according to claim 1, wherein the content of epichlorohydrin is greater than or equal to 999 g/kg of product.

14. The product according to claim 1, wherein the content of epichlorohydrin is greater than or equal to 999.5 g/kg of product.

15. The product according to claim 3, wherein the chloroalkoxypropanol is chloromethoxypropanol.

16. The product according to claim 4, wherein the chloroalkoxypropanol is selected from the group consisting of 2-chloro-3-methoxy-propane-1-ol, 1-chloro-3-methoxy-propane-2-ol, and mixtures thereof.

17. The product according to claim 5, wherein the glycerol alkyl ether is glycerol methyl ether.

18. The process according to claim 6, wherein the chloro alkoxy propanol is chloromethoxypropanol.

19. The process of claim 7, wherein the glycerol alkyl ether is glycerol methyl ether.

* * * * *

UNITED STATES PATENT AND TRADEMARK OFFICE
CERTIFICATE OF CORRECTION

PATENT NO. : 8,378,130 B2  
APPLICATION NO. : 12/663744  
DATED : February 19, 2013  
INVENTOR(S) : Noel Boulos et al.

Page 1 of 1

It is certified that error appears in the above-identified patent and that said Letters Patent is hereby corrected as shown below:

On the title page, Item (86), the PCT Item (86) should read:

--(86) PCT No.:     PCT/EP2008/057246

§ 371(c)(1),  
(2), (4) Date:     Dec. 9, 2009--

Signed and Sealed this  
Twenty-third Day of April, 2013

Teresa Stanek Rea  
*Acting Director of the United States Patent and Trademark Office*